(12) United States Patent
Sueda et al.

(10) Patent No.: US 9,339,445 B2
(45) Date of Patent: *May 17, 2016

(54) HEXAGONAL PLATE-SHAPED ZINC OXIDE PARTICLES, METHOD FOR PRODUCTION OF THE SAME, AND COSMETIC, HEAT RELEASING FILLER, HEAT RELEASING RESIN COMPOSITION, HEAT RELEASING GREASE, AND HEAT RELEASING COATING COMPOSITION COMPRISING THE SAME

(75) Inventors: Satoru Sueda, Fukushima (JP); Mitsuo Hashimoto, Fukushima (JP); Atsuki Terabe, Fukushima (JP); Nobuo Watanabe, Fukushima (JP); Koichiro Magara, Fukushima (JP)

(73) Assignee: Sakai Chemical Industry Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/113,115

(22) PCT Filed: Apr. 26, 2012

(86) PCT No.: PCT/JP2012/061280
§ 371 (c)(1),
(2), (4) Date: Nov. 4, 2013

(87) PCT Pub. No.: WO2012/147886
PCT Pub. Date: Nov. 1, 2012

(65) Prior Publication Data
US 2014/0050925 A1 Feb. 20, 2014

(30) Foreign Application Priority Data
Apr. 28, 2011 (JP) ................. 2011-101021

(51) Int. Cl.
*C01G 9/02* (2006.01)
*B32B 5/16* (2006.01)
(Continued)

(52) U.S. Cl.
CPC ........... *A61K 8/0254* (2013.01); *A61K 8/27* (2013.01); *A61Q 1/02* (2013.01); *A61Q 17/04* (2013.01);
(Continued)

(58) Field of Classification Search
CPC ............ C01P 2004/39; C01P 2004/54; Y10T 428/2982; C01G 9/02
USPC ............................ 428/402; 106/425; 423/622
See application file for complete search history.

(56) References Cited

U.S. PATENT DOCUMENTS

| | | | |
|---|---|---|---|
| 5,093,099 A | 3/1992 | Haishi et al. | |
| 2002/0018885 A1* | 2/2002 | Takahashi et al. | ............ 428/328 |

(Continued)

FOREIGN PATENT DOCUMENTS

| | | |
|---|---|---|
| JP | H07-187673 A | 7/1995 |
| JP | H09-137152 A | 5/1997 |

(Continued)

OTHER PUBLICATIONS

Garcia, S.P., et al., "Controlling the Morphology of Zinc Oxide Nanorods Crystallized from Aqueous Solutions: The Effect of Crystal Growth Modifiers on Aspect Ratio", Chemistry of Materials, 2007, 19, pp. 4016-4022.

(Continued)

Primary Examiner — Holly Le
(74) Attorney, Agent, or Firm — Polsinelli PC

(57) ABSTRACT

An object of the present invention is to provide hexagonal plate-shaped zinc oxide particles which can be used as a cosmetic raw material, a heat releasing filler and the like, a method for production of the same, and a cosmetic, a heat releasing filler, a heat releasing resin composition, a heat releasing grease and a heat releasing coating composition each comprising the same. Provided are hexagonal plate-shaped zinc oxide particles having hexagonal-shaped surfaces, wherein the primary particle diameter is 0.01 μm or more and the aspect ratio is 2.5 or more, and 50% or more of 250 particles in a transmission electron microscope photograph satisfy both the requirements (1) the particle has a hexagonal-shaped surface; and (2) Dmin/Dmax≥0.3, where Dmax: a length of the largest diagonal line of three diagonal lines of the hexagonal-shaped surface of the hexagonal plate-shaped zinc oxide particle; and Dmin: a length of the smallest diagonal line of three diagonal lines of the hexagonal-shaped surface of the hexagonal plate-shaped zinc oxide particle.

14 Claims, 11 Drawing Sheets

(51) Int. Cl.
*A61K 8/02* (2006.01)
*C09C 1/04* (2006.01)
*C09D 7/12* (2006.01)
*A61K 8/27* (2006.01)
*A61Q 1/02* (2006.01)
*A61Q 17/04* (2006.01)
*A61Q 19/00* (2006.01)
*C09K 5/14* (2006.01)
*B82Y 30/00* (2011.01)
*C08K 3/22* (2006.01)

(52) U.S. Cl.
CPC ............... *A61Q 19/00* (2013.01); *B82Y 30/00* (2013.01); *C01G 9/02* (2013.01); *C08K 3/22* (2013.01); *C09C 1/043* (2013.01); *C09D 7/1216* (2013.01); *C09D 7/1266* (2013.01); *C09D 7/1291* (2013.01); *C09K 5/14* (2013.01); *C01P 2002/72* (2013.01); *C01P 2004/03* (2013.01); *C01P 2004/04* (2013.01); *C01P 2004/20* (2013.01); *C01P 2004/22* (2013.01); *C01P 2004/51* (2013.01); *C01P 2004/54* (2013.01); *C01P 2004/62* (2013.01); *C01P 2004/64* (2013.01); *C08K 2003/2296* (2013.01); *Y10T 428/2982* (2015.01)

(56) References Cited

U.S. PATENT DOCUMENTS

| | | | |
|---|---|---|---|
| 2007/0154561 A1* | 7/2007 | Takeda et al. | 424/489 |
| 2011/0081548 A1 | 4/2011 | Sueda et al. | |
| 2011/0081550 A1 | 4/2011 | Sueda et al. | |
| 2011/0150792 A1* | 6/2011 | Shao et al. | 424/59 |
| 2014/0044971 A1* | 2/2014 | Sueda et al. | 428/402 |
| 2014/0058029 A1* | 2/2014 | Sueda et al. | 524/432 |
| 2014/0112862 A1* | 4/2014 | Sueda et al. | 423/622 |

FOREIGN PATENT DOCUMENTS

| | | |
|---|---|---|
| JP | 2001-163619 A | 6/2001 |
| JP | 2002194379 A | 7/2002 |
| JP | 2007-223874 A | 9/2007 |
| WO | WO-2010/050430 A1 | 5/2010 |

OTHER PUBLICATIONS

Meagley et al., "Chemical Control of Crystal Growth with Multidentate Carboxylate Ligands: Effect of Ligand Denticity on Zinc Oxide Crystal Shape", Cryst. Growth Des., 2012, 12, 707-713.

* cited by examiner

FIG.24

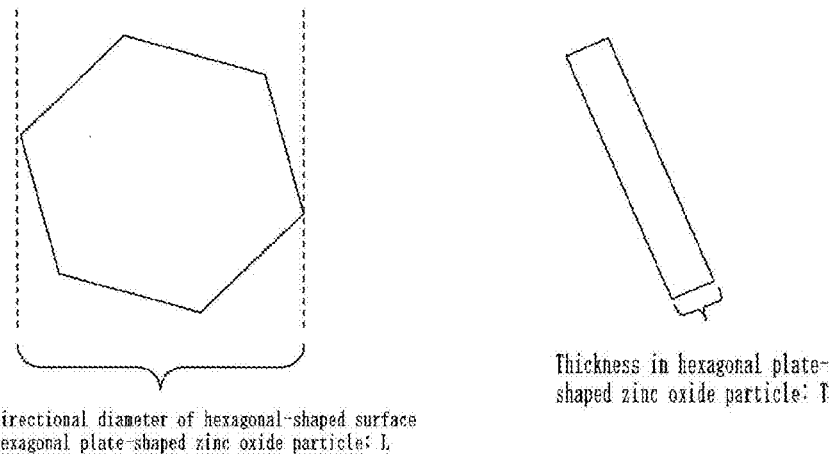

Unidirectional diameter of hexagonal-shaped surface in hexagonal plate-shaped zinc oxide particle: L Thickness in hexagonal plate-shaped zinc oxide particle: T Aspect ratio of hexagonal plate-shaped zinc oxide particles = (average value of unidirectional diameters of hexagonal-shaped surfaces of 250 particles: L)/(average value of thicknesses of 250 particles: T)

FIG.25

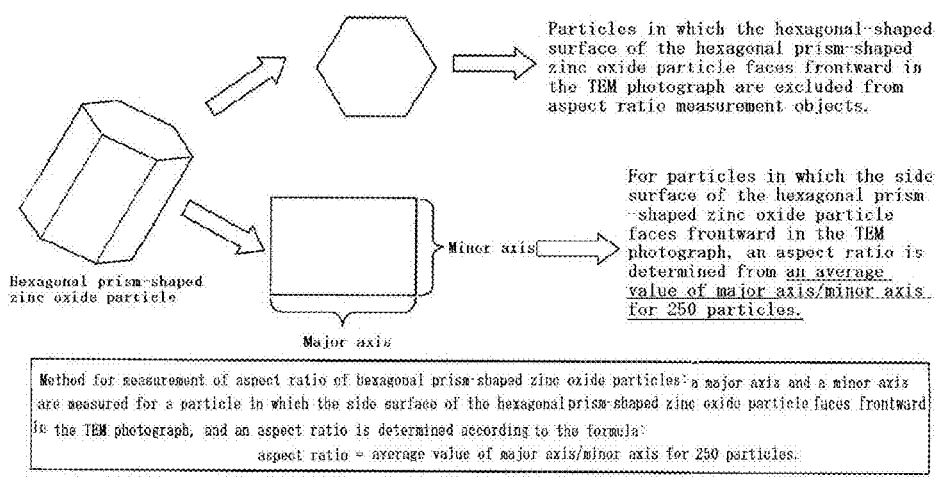

Hexagonal prism-shaped zinc oxide particle

Particles in which the hexagonal-shaped surface of the hexagonal prism-shaped zinc oxide particle faces frontward in the TEM photograph are excluded from aspect ratio measurement objects.

For particles in which the side surface of the hexagonal prism-shaped zinc oxide particle faces frontward in the TEM photograph, an aspect ratio is determined from an average value of major axis/minor axis for 250 particles.

Method for measurement of aspect ratio of hexagonal prism-shaped zinc oxide particles: a major axis and a minor axis are measured for a particle in which the side surface of the hexagonal prism-shaped zinc oxide particle faces frontward in the TEM photograph, and an aspect ratio is determined according to the formula:
aspect ratio = average value of major axis/minor axis for 250 particles.

FIG.26

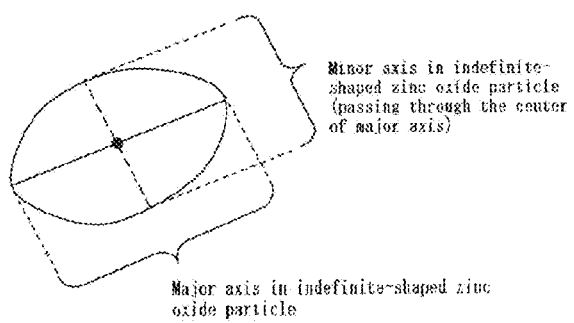

Method for measurement of aspect ratio of zinc oxide particles having an indefinite shape: a major axis and a minor axis passing through the center of the major axis are measured for an indefinite-shaped zinc oxide particle in the TEM photograph, and an aspect ratio is determined according to the formula:
aspect ratio = average value of major axis/minor axis for 250 particles.

HEXAGONAL PLATE-SHAPED ZINC OXIDE PARTICLES, METHOD FOR PRODUCTION OF THE SAME, AND COSMETIC, HEAT RELEASING FILLER, HEAT RELEASING RESIN COMPOSITION, HEAT RELEASING GREASE, AND HEAT RELEASING COATING COMPOSITION COMPRISING THE SAME

CROSS REFERENCE TO RELATED APPLICATIONS

This application is a National Phase filing under 35 U.S.C. §371 of PCT/JP2012/061280 filed on Apr. 26, 2012; and this application claims priority to Application No. 2011-101021 filed in Japan on Apr. 28, 2011, under 35 U.S.C. §119; the entire contents of all are hereby incorporated by reference.

TECHNICAL FIELD

The present invention relates to hexagonal plate-shaped zinc oxide particles, a method for production of the same, and a cosmetic, a heat releasing filler, a heat releasing resin composition, a heat releasing grease and a heat releasing coating composition each containing the same.

BACKGROUND OF THE DISCLOSURE

Zinc oxide particles, which have been used as a sunscreen ultraviolet blocking agent in cosmetic product applications, are ultrafine particles having an average particle diameter of 0.1 μm or less, and have a particle shape that is not controlled to be a hexagonal plate-shape. However, such conventional zinc oxide ultrafine particles for ultraviolet blocking deteriorate slippage, and are therefore hardly used for cosmetics in which comfort in use is important, such as foundations and other make-up cosmetics. Such make-up cosmetics generally contain plate-shaped particles such as those of talc, mica and barium sulfate.

However, these plate-shaped particles do not have an ultraviolet blocking effect, and therefore for imparting ultraviolet blocking performance, zinc oxide fine particles or titanium oxide fine particles in an amount small enough that slippage is not hindered, or an organic ultraviolet blocking agent must be used in combination. Accordingly, presence of plate-shaped zinc oxide particles having proper slippage is preferable because slippage and ultraviolet blocking performance can be imparted with one kind of particles.

In recent years, cosmetics having an effect of blurring a base when applied to the skin (a so called soft focus effect) have been known. However, no attempt has been made to obtain such a soft focus effect with zinc oxide particles.

In sunscreen cosmetic applications, zinc oxide fine particles having a particle diameter of 0.1 μm or less have been used. However, such zinc oxide fine particles have the disadvantage that they are poor in soft focus effect, and lack an effect of blurring a base.

As hexagonal plate-shaped zinc oxide, those in Patent Documents 1 to 3 are known. However, the zinc oxide particles in Patent Document 1 are formed by aggregation of zinc oxide fine particles in a hexagonal plate shape, and therefore proper slippage cannot be achieved. Further, since the particle shape is not sufficiently controlled, physical properties tend to vary, so that it is difficult to obtain a cosmetic with stable quality.

Patent Document 2 describes flaky plate-shaped zinc oxide particles, and uses thereof in cosmetics and industrial applications. However, many of the flaky plate-shaped zinc oxide particles described in Patent Document 2 have a large particle diameter, and the particle shape is not controlled to be fine and uniform. In the production method, a basic zinc salt is generated, and therefore a thermal decomposition step such as that of calcinating is required to obtain zinc oxide.

Patent Document 3 describes hexagonal plate-shaped zinc oxide particles. However, the zinc oxide particles in Patent Document 3 significantly vary in particle diameter and shape, and are aggregated, so that problems such as those described above cannot be sufficiently rectified.

In applications of heat releasing materials in electronic/electrical fields, aluminum oxide, aluminum nitride, boron nitride, zinc oxide and the like are often used as a heat releasing filler. It is generally known that two or more kinds of spherical particles having different particle diameters are filled, and a filler is filled in a resin or the like at a high rate for achieving high heat releasing performance. Meanwhile, it is considered to make use of anisotropy of thermal conduction by compounding particles of different shapes, such as plate-shaped particles and needle-shaped particles, for more effectively enhancing heat conductivity. However, the zinc oxide particles in Patent Document 1 are aggregates, and therefore influences of heat resistance between particles in plate-shaped particles are significant, so that anisotropy of thermal conduction specific to plate-shaped particles cannot be exhibited.

Usually, in production of zinc oxide particles, mostly a calcinating step is essential. In calcinating, however, equipment capable of performing a treatment at a high temperature is required, and there is the problem that the particle diameter and the particle shape which have been adjusted/controlled in the stage of a zinc oxide precursor are changed by calcinating, and so on. Therefore, it is very preferable to obtain zinc oxide particles without performing calcinating.

PRIOR TECHNICAL DOCUMENTS

Patent Documents

[Patent Document 1] Japanese Kokai Publication 2007-223874
[Patent Document 2] Japanese Kokai Publication Hei7-187673
[Patent Document 3] Japanese Kokai Publication Hei9-137152

SUMMARY OF INVENTION

Problems to be Solved by the Invention

In view of the situations described above, it is an object of the present invention to provide hexagonal plate-shaped zinc oxide particles which can be used as a cosmetic raw material, a heat releasing filler and the like, a method for production of the same, and a cosmetic, a heat releasing filler, a heat releasing resin composition, a heat releasing grease and a heat releasing coating composition each comprising the same. Further, it is an object of the present invention to provide a method for production of zinc oxide particles, which does not include a calcinating step.

Means for Solving Object

The present invention provides hexagonal plate-shaped zinc oxide particles having hexagonal-shaped surfaces, wherein the primary particle diameter is 0.01 μm or more and the aspect ratio is 2.5 or more, and 50% or more of 250 particles in a transmission electron microscope photograph satisfy both the requirements (1) and (2):

(1) the particle has a hexagonal-shaped surface; and
(2) Dmin/Dmax≥0.3, where

Dmax: a length of the largest diagonal line of three diagonal lines of the hexagonal-shaped surface of the hexagonal plate-shaped zinc oxide particle; and Dmin: a length of the smallest diagonal line of three diagonal lines of the hexagonal-shaped surface of the hexagonal plate-shaped zinc oxide particle.

The hexagonal plate-shaped zinc oxide particles of the present invention are preferably those obtained by aging zinc oxide fine particles in an aqueous zinc salt solution.

The present invention also provides a method for production of the hexagonal plate-shaped zinc oxide particles described above, comprising a step of aging zinc oxide fine particles in an aqueous zinc salt solution.

The present invention also provides a cosmetic containing the hexagonal plate-shaped zinc oxide particles described above.

The present invention also provides a heat releasing filler made of the hexagonal plate-shaped zinc oxide particles described above.

The present invention also provides a heat releasing resin composition containing the hexagonal plate-shaped zinc oxide particles described above.

The present invention also provides a heat releasing grease containing the hexagonal plate-shaped zinc oxide particles described above.

The present invention also provides a heat releasing coating composition containing the hexagonal plate-shaped zinc oxide particles described above.

Effects of the Invention

The zinc oxide particles of the present invention have excellent comfort in use and ultraviolet blocking performance when compounded in a cosmetic. The zinc oxide particles can be made to have a soft focus effect or transparency depending on the particle diameter. The zinc oxide particles exhibit excellent heat releasing performance when used as a heat releasing filler.

BRIEF DESCRIPTION OF THE DRAWINGS

FIG. 24 is a schematic view illustrating a method for measurement of an aspect ratio of zinc oxide particles of the present invention in claim 1.

FIG. 25 is a schematic view illustrating a method for measurement of an aspect ratio of hexagonal prism-shaped zinc oxide particles of a comparative example.

FIG. 26 is a schematic view illustrating a method for measurement of an aspect ratio of indefinite-shaped zinc oxide particles of comparative examples.

DETAILED DESCRIPTION OF PREFERRED EMBODIMENTS

Figure 1:
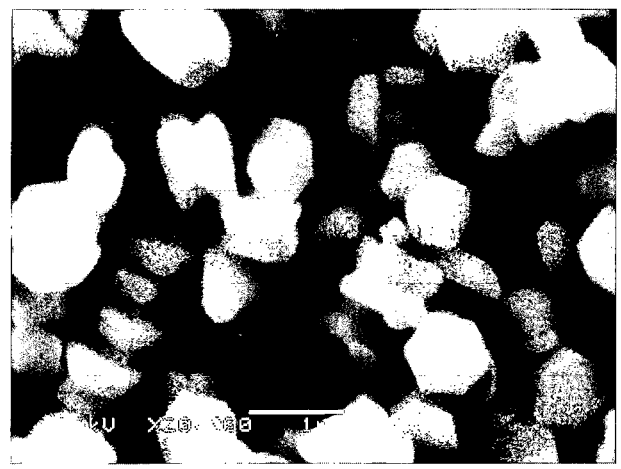
FIG. 1 is a scanning electron microscope photograph of zinc oxide particles of the present invention obtained in Example 1.

The present invention will be described in detail hereinafter.

The hexagonal plate-shaped zinc oxide particles of the present invention can be suitably used as a powder for cosmetics because their primary particles have a shape close to a regular hexagon, and the level of aggregation is low. Particularly when hexagonal plate-shaped zinc oxide particles having a particle diameter of 0.3 µm or more, among those described above, are used, the haze is increased to enhance an effect of blurring a base (a so called soft focus effect). The hexagonal plate-shaped zinc oxide particles of the present invention having a particle diameter in the above-mentioned range have a haze higher than that of general zinc oxide having a similar particle diameter although their total light transmittances are almost equal. This means that those hexagonal plate-shaped zinc oxide particles have high light scattering efficiency, leading to a high soft focus effect when they are applied to the skin. Hexagonal plate-shaped zinc oxide particles of 0.5 µm or more are suitably used as particles in foundation applications because very good slippage and excellent comfort in use are provided.

On the other hand, hexagonal plate-shaped zinc oxide particles of less than 0.3 µm are suitably used as an ultraviolet blocking agent in sunscreen agent applications because the parallel light transmittance is enhanced to achieve excellent transparency. Further, those hexagonal plate-shaped zinc oxide particles have excellent ultraviolet blocking performance because they are composed of zinc oxide.

Further, the crystal structure of zinc oxide is a wurtzite-type crystal structure where a zinc ion is surrounded by four oxygen ions in the form of a regular tetrahedron. Four distances between zinc ion and oxygen ions in an actual crystal of zinc oxide are not equal, and only a distance between a zinc ion and an oxygen ion, which is in parallel relation to the c axis direction (direction vertical to the plate-shaped surface; thickness direction), is 0.1991 nm and slightly longer than other bonding distances, i.e. 0.1976 nm. Accordingly, the bond in the c axis direction of zinc oxide is slightly weak, and thermal conduction by thermal vibration (phonon) in the c axis direction is slow. Conversely, thermal conduction in the a axis direction (plate-shaped surface direction) and the b axis direction (plate-shaped surface direction) is fast because the bonding distance is shorter than that in the c axis direction. That is, hexagonal plate-shaped zinc oxide particles grown in the a axis and b axis directions, which are obtained in the present invention, can exhibit anisotropy of thermal conduction to obtain a proper thermal conductivity as the plate-shaped surface is oriented in parallel to the direction of heat transmission. Therefore, it is thought that the hexagonal plate-shaped zinc oxide particles can be suitably used as a heat releasing material.

The zinc oxide particles of the present invention are hexagonal plate-shaped zinc oxide particles having hexagonal-shaped surfaces, wherein the primary particle diameter is 0.01 µm or more and the aspect ratio is 2.5 or more, and 50% or more of 250 particles in a transmission electron microscope photograph satisfy both the requirements (1) and (2):

(1) the particle has a hexagonal-shaped surface; and
(2) Dmin/Dmax≥0.3, where

Dmax: a length of the largest diagonal line of three diagonal lines of the hexagonal-shaped surface of the hexagonal plate-shaped zinc oxide particle; and Dmin: a length of the smallest diagonal line of three diagonal lines of the hexagonal-shaped surface of the hexagonal plate-shaped zinc oxide particle.

The hexagonal plate-shaped zinc oxide particles of the present invention are zinc oxide particles having a primary particle diameter of 0.01 µm or more and having a fine hexagonal plate shape. By appropriately controlling the primary particle diameter of the hexagonal plate-shaped zinc oxide particles of the present invention, various kinds of performance such as proper slippage, a soft focus effect, ultraviolet blocking performance, and transparency to visible light can be selectively imparted. The primary particle diameter is more preferably 0.02 µm or more, further preferably 0.03 µm or more. The upper limit of the primary particle diameter is not particularly limited, but is, for example, preferably 100 µm or less, more preferably 50 µm or less, further preferably 25 µm or less.

Figure 23:
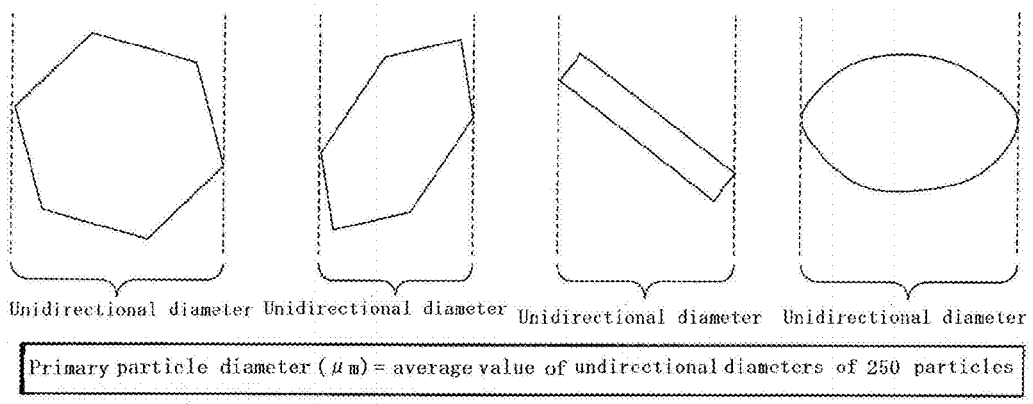
FIG. 23 is a schematic view illustrating a method for measurement of a primary particle diameter of zinc oxide particles of the present invention in claim 1.

The primary particle diameter herein is a particle diameter (µm) defined by a unidirectional diameter in a visual field of 2000 to 50000 magnification in a transmission electron microscope (TEM, JEM-1200EX II, manufactured by JEOL Ltd.) photograph (distance between two parallel lines in a fixed direction with a particle held therebetween; measurements are made in a fixed direction regardless of shapes of particles on the image), and is obtained by measuring the unidirectional diameters of 250 primary particles in the TEM photograph and determining an average value of a cumulative distribution thereof. For the method for measurement of a primary particle diameter, FIG. 23 is attached.

Further, the hexagonal plate-shaped zinc oxide particles of the present invention have an aspect ratio of 2.5 or more. That is, the hexagonal plate-shaped zinc oxide particles are zinc oxide particles having a hexagonal plate shape, and particularly when they are used for a cosmetic, good slippage and excellent comfort in use can be achieved owing to the above-mentioned shape. The aspect ratio of the hexagonal plate-shaped zinc oxide particles in the present invention is a value determined as a ratio of L/T where L is an average value of measured particle diameters (µm) of 250 particles, the particle diameter defined by a unidirectional diameter for particles in which the hexagonal-shaped surface of the hexagonal plate-shaped zinc oxide particle faces frontward (distance between two parallel lines in a fixed direction with a particle held therebetween; measurements are made in a fixed direction for particles in which the hexagonal-shaped surface on the image faces frontward), and T is an average value of measured thicknesses (µm) (length of the shorter side of rectangle) of 250 particles for particles in which the side surface of the hexagonal plate-shaped zinc oxide particle faces frontward (particles that appear rectangular), in a visual field of 2000 to 50000 magnification in a transmission electron microscope (TEM, JEM-1200EX II, manufactured by JEOL Ltd.) photograph or a scanning electron microscope (SEM, JSM-5600, manufactured by JEOL Ltd.) photograph. For the method for measurement of an aspect ratio, FIG. 24 is attached. The aspect ratio is more preferably 2.7 or more, further preferably 3.0 or more.

The zinc oxide particles of the present invention are hexagonal plate-shaped zinc oxide particles having hexagonal-shaped surfaces, wherein 50% or more of 250 particles in a transmission electron microscope photograph satisfy both the requirements (1) and (2):

(1) the particle has a hexagonal-shaped surface; and
(2) Dmin/Dmax≥0.3, where

Dmax: a length of the largest diagonal line of three diagonal lines of the hexagonal-shaped surface of the hexagonal plate-shaped zinc oxide particle; and Dmin: a length of the smallest diagonal line of three diagonal lines of the hexagonal-shaped surface of the hexagonal plate-shaped zinc oxide particle.

Where Dmax is a length of a diagonal line of a regular hexagon, Dmin/Dmax denotes a deviation from the length of the diagonal line of the regular hexagon, and the deviation decreases as the value becomes closer to 1, while the deviation increases as the value becomes closer to 0. Dmin/Dmax is 0.3 or more, but is preferably 0.5 or more, further preferably 0.7 or more.

Figure 22:
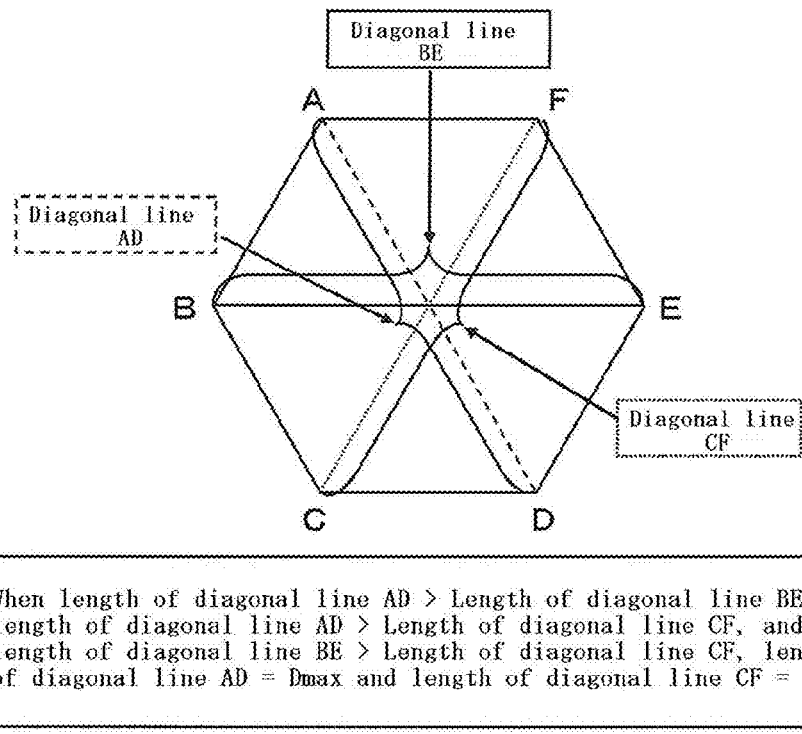
FIG. 22 is a schematic view illustrating the parameter (2) of zinc oxide particles of the present invention according to claim 1.

In the definition described above, three diagonal lines denote a diagonal line AD connecting A and D, a diagonal line BE connecting B and E and a diagonal line CF connecting C and F where one apex of the hexagon in the hexagonal-shaped surface is A and other apexes are B, C, D, E and F in order with B adjacent to A. Of the diagonal lines AD, BE and CF, the length of the longest diagonal line is defined as Dmax and the length of the shortest diagonal line is defined as Dmin. These parameters are schematically shown in FIG. 22 for easy understanding.

Measurements of the values of the parameters described above were made on the basis of a transmission electron microscope photograph, and Dmax and Dmin were measured using a ruler.

The parameters (1) and (2) described above are measured for 250 particles in a transmission electron microscope photograph. In the measurement described above, all particles including not only particles observed in terms of a hexagonal-shaped surface but also particles observed in terms of a side surface in the image are counted. In the zinc oxide particles of the present invention, 50% or more of 250 particles in the transmission electron microscope photograph satisfy the parameters (1) and (2) described above.

Zinc oxide particles that satisfy the parameters have particularly good performance.

In the hexagonal plate-shaped zinc oxide particles of the present invention, 50% or more of 250 particles in the transmission electron microscope photograph satisfy the parameters (1) and (2) described above. The above-described effect of the present invention is not achieved unless at least 50% of the particles satisfy the parameters. Preferably 55% or more of the particles satisfy the parameters, and further preferably 60% or more of the particles satisfy the parameters.

For the hexagonal plate-shaped zinc oxide particles of the present invention which are obtained in Examples described later, Dmin/Dmax values of 250 particles were measured also for only particles observed in terms of a hexagonal-shaped surface, and an average value thereof was determined. The results are shown in Table 1.

The method for production of zinc oxide particles having the shape described above is not particularly limited, and they can be obtained by, for example, a production method including a step of aging zinc oxide fine particles in an aqueous zinc salt solution. Such a method for production of zinc oxide particles is a part of the present invention. By such a method for production of zinc oxide particles, the hexagonal plate-shaped zinc oxide particles of the present invention as described above can be directly obtained without going through a step of thermal decomposition such as that of calcinating. Further, zinc oxide particles having a high zinc oxide purity can be obtained. However, calcinating may be performed for the purpose of enhancing crystallinity, and so on.

In production of hexagonal plate-shaped zinc oxide particles as described above, zinc oxide fine particles are used. The zinc oxide fine particle is not particularly limited, but its particle diameter is preferably 0.005 μm or more and 0.05 μm or less. The particle diameter of the zinc oxide fine particle corresponds to a diameter of a sphere having the same surface area as a specific surface area determined by a BET method. That is, the particle diameter is a value determined by the following calculation formula from a specific surface area: Sg determined by making a measurement using a fully automatic BET specific surface area measuring device Macsorb (manufactured by Mountech Co., Ltd.), and a true specific gravity of zinc oxide: ρ.

$$\text{particle diameter}(\mu m) = [6/(Sg \times \rho)]$$

(Sg (m$^2$/g): specific surface area, ρ (g/cm$^3$): true specific gravity of particle)

As the true specific gravity of particle: ρ, a value of the true specific gravity of zinc oxide, i.e. 5.6, was used for the above calculation.

Zinc oxide fine particles that can be used as a raw material are not particularly limited, and zinc oxide produced by a known method can be used. Examples of those that are commercially available may include FINEX-75, FINEX-50 and FINEX-30 manufactured by Sakai Chemical Industry Co., Ltd.

In the method for production of hexagonal plate-shaped zinc oxide particles according to the present invention, the zinc oxide fine particles described above are aged in an aqueous zinc salt solution. That is, the zinc oxide fine particles are dispersed in an aqueous zinc salt solution, and heated in this state to be crystal-grown.

The solvent to be used in the present invention is water. Water is inexpensive and safe in terms of handling, and is therefore most preferable from the viewpoint of production control and costs.

The aqueous zinc salt solution to be used is not particularly limited, and examples thereof may include aqueous solutions of zinc acetate, zinc nitrate, zinc sulfate, zinc chloride and zinc formate. Particularly when an aqueous zinc acetate solution, among the aqueous zinc salt solutions, is used, specific hexagonal plate-shaped zinc oxide particles of the present invention can be suitably obtained.

These aqueous zinc salt solutions may be those prepared by mixing zinc oxide, an acid and water to acid-hydrolyze zinc oxide. The particle shape and particle size of zinc oxide to be used when the aqueous zinc salt solution is prepared with zinc oxide, an acid and water are not particularly limited, but the Zn purity of zinc oxide is preferably 95% or more for reducing impurities as much as possible. Examples of the acid include acetic acid, nitric acid, sulfuric acid, hydrochloric acid, formic acid, citric acid, oxalic acid, propionic acid, malonic acid, lactic acid, tartaric acid, gluconic acid and succinic acid, and particularly when acetic acid is used, specific hexagonal plate-shaped zinc oxide particles of the present invention can be suitably obtained. Two of these aqueous zinc salt solutions may be used in combination.

The zinc salt concentration in the aqueous zinc salt solution is preferably more than 0.45 mol/l and 4.00 mol/l or less, and particularly the zinc salt concentration in the aqueous zinc acetate solution is preferably more than 0.45 mol/l and 2.00 mol/l or less.

When zinc oxide fine particles are added in the aqueous zinc salt solution to form a slurry, the concentration of zinc oxide fine particles is preferably 10 to 500 g/l based on the total amount of the slurry.

The method for preparation of a slurry is not particularly limited, and for example, a homogeneous slurry having a zinc oxide fine particle concentration of 10 to 500 g/l can be formed by adding the above-described components to water, and dispersing the components at 5 to 30° C. for 10 to 30 minutes.

In the aging described above, components other than zinc oxide fine particles, a zinc salt and water may be added in a small amount within the bounds of not impairing the effect of the present invention. For example, a dispersant and the like may be added.

Preferably, aging is performed at 45 to 110° C. The aging time may be 0.5 to 24 hours. The particle diameter can be adjusted by conditions such as an aging temperature, an aging time, a zinc oxide fine particle concentration and a zinc salt concentration, and therefore it is preferable to appropriately set these conditions according to intended hexagonal plate-shaped zinc oxide particles.

Hexagonal plate-shaped zinc oxide particles thus obtained may be subjected to post-treatments such as filtration, water washing and drying as necessary.

Hexagonal plate-shaped zinc oxide particles produced by the above-described method may be classified by sieving as necessary. Examples of methods for classification by sieving may include wet classification and dry classification. Further, a treatment such as wet crushing or dry crushing may be performed.

As described above, the method for production of hexagonal plate-shaped zinc oxide particles according to the present invention is capable of obtaining zinc oxide particles without performing a calcinating treatment, but hexagonal plate-shaped zinc oxide particles obtained by the above-described method may be subjected to a calcinating treatment. For calcinating, mention may be made of a known method using an arbitrary device, and treatment conditions and the like are not particularly limited.

The hexagonal plate-shaped zinc oxide particles of the present invention may be further surface-treated as necessary. The surface treatment is not particularly limited, and examples thereof may include known treatment methods such as inorganic surface treatments to form an inorganic oxide layer such as a silica layer, an alumina layer, a zirconia layer or a titania layer, and various kinds of other surface treatments. Two or more kinds of surface treatments may be sequentially performed.

More specific examples of the surface treatment may include surface treatments with a surface treatment agent selected from an organic silicon compound, an organic aluminum compound, an organic titanium compound, a higher fatty acid, a higher fatty acid ester, a metallic soap, a polyhydric alcohol and an alkanolamine. For the surface treatment agent described above, a treatment amount can be appropriately set according to the particle diameter of the hexagonal plate-shaped zinc oxide particle.

Examples of the organic silicon compound may include organopolysiloxanes such as methyl hydrogen polysiloxane and dimethyl polysiloxane, and silane coupling agents such as triethoxyvinylsilane and diphenyldimethoxysilane.

Examples of the higher fatty acid may include higher fatty acids having 10 to 30 carbon atoms, such as lauric acid, stearic acid and palmitic acid.

Examples of the higher fatty acid ester may include alkyl esters of the above-described higher fatty acids, such as octyl palmitate.

Examples of the metallic soap may include metal salts of the above-described higher fatty acids, such as aluminum stearate and aluminum laurate. The metal species that forms the metallic soap is not particularly limited, and examples thereof may include aluminum, lithium, magnesium, calcium, strontium, barium, zinc and tin.

Examples of the polyhydric alcohol may include trimethylolethane, trimethylolpropane and pentaerythritol.

Examples of the alkanolamine may include diethanolamine, dipropanolamine, triethanolamine and tripropanolamine.

The treatment with the surface treatment agent can be achieved by mixing a predetermined amount of the surface treatment agent with the hexagonal plate-shaped zinc oxide particles. Further, the treatment can be achieved by adding the hexagonal plate-shaped zinc oxide particles to an appropriate medium, for example, water, an alcohol, an ether or the like to be suspended, adding a surface treatment agent to the suspension, followed by stirring, separating, drying and crushing the suspension, or solidifying by evaporation and crushing the suspension.

Since hexagonal plate-shaped zinc oxide particles subjected to the surface treatment described above have various kinds of coating layers such as those of zinc silicate on the surfaces thereof, the physiological activity and chemical activity thereof are suppressed when the zinc oxide particles are compounded in a cosmetic, and therefore a particularly excellent cosmetic product can be provided.

The hexagonal plate-shaped zinc oxide particles of the present invention are not particularly limited for applications thereof, and can be suitably used in, for example, applications of raw materials of cosmetics and heat releasing fillers. These cosmetics and heat releasing fillers are apart of the present invention.

A cosmetic containing the hexagonal plate-shaped zinc oxide particles of the present invention has the advantage of ultraviolet blocking performance and good comfort in use because the zinc oxide particles are in the shape of a plate. Further, the cosmetic has the advantage that it has a soft focus effect when used as a cosmetic.

Examples of the cosmetic of the present invention may include a foundation, a makeup base, an eye shadow, a rouge, a mascara, a lipstick and a sunscreen agent. The cosmetic of the present invention can be in any form such as that of an oily cosmetic, an aqueous cosmetic, an O/W type cosmetic or a W/O type cosmetic.

For the cosmetic of the present invention, any aqueous component or oily component that can be used in the field of cosmetics can be used in combination in addition to components that form the above-described mixture. The aqueous component and oily component described above are not particularly limited, and examples thereof may include those containing components such as oils, surfactants, moisturizers, higher alcohols, sequestrants, natural and synthetic polymers, water-soluble and oil-soluble polymers, UV blocking agents, various extracts, inorganic and organic pigments, inorganic and organic clay minerals, inorganic and organic pigments treated with metallic soap or silicone, coloring materials such as organic dyes, preservatives, antioxidants, dyes, thickeners, pH adjusters, perfumes, cooling-sensation agents, antiperspirants, disinfectants, and skin activators. Specifically, a desired cosmetic can be produced in the usual manner using any one or more of the components listed below. The amounts of these components incorporated are not particularly restricted as long as they do not interfere with the effects of the present invention.

The oil is not particularly limited, and examples thereof may include avocado oil, camellia oil, turtle oil, macadamia nut oil, corn oil, mink oil, olive oil, rapeseed oil, egg-yolk oil, sesame oil, persic oil, wheat germ oil, sasanqua oil, castor oil, linseed oil, safflower oil, cottonseed oil, perilla oil, soybean oil, arachis oil, tea seed oil, kaya oil, rice bran oil, Chinese tung oil, Japanese tung oil, jojoba oil, germ oil, triglycerol, glycerol trioctanoate, glycerol triisopalmitate, cacao butter, coconut oil, horse fat, hydrogenated coconut oil, palm oil, beef tallow, mutton tallow, hydrogenated beef tallow, palm kernel oil, lard, beef bone fat, Japan wax kernel oil, hydrogenated oil, neatsfoot oil, Japan wax, hydrogenated castor oil, beeswax, candelilla wax, cotton wax, carnauba wax, bayberry wax, insect wax, spermaceti wax, montan wax, bran wax, lanolin, kapok wax, lanolin acetate, liquid lanolin, sugarcane wax, isopropyl lanolate, hexyl laurate, reduced lanolin, jojoba wax, hard lanolin, shellac wax, POE lanolin alcohol ether, POE lanolin alcohol acetate, POE cholesterol ether, polyethylene glycol lanolate, POE hydrogenated lanolin alcohol ether, liquid paraffin, ozokerite, pristane, paraffin, ceresin, squalene, Vaseline, and microcrystalline wax.

The lipophilic nonionic surfactant is not particularly limited, and examples thereof may include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; glycerin polyglycerin fatty acids such as glycerol mono-cottonseed oil fatty acid, glycerol monoerucate, glycerol sesquioleate, glycerol monostearate, α,α'-glycerol oleate pyroglutamate, and glycerol monostearate malate; propylene glycol fatty acid esters such as propylene glycol monostearate; hydrogenated castor oil derivatives; and glycerol alkyl ethers.

The hydrophilic nonionic surfactant is not particularly limited, and examples thereof may include POE sorbitan fatty acid esters such as POE sorbitan monostearate, POE sorbitan monooleate and POE sorbitan tetraoleate; POE sorbitol fatty acid esters such as POE sorbitol monolaurate, POE sorbitol monooleate, POE sorbitol pentaoleate and POE sorbitol monostearate; POE glycerin fatty acid esters such as POE glycerin monostearate, POE glycerin monoisostearate and POE glycerin triisostearate; POE fatty acid esters such as POE monooleate, POE distearate, POE monodioleate and ethylene glycol distearate; POE alkyl ethers such as POE lauryl ether, POE oleyl ether, POE stearyl ether, POE behenyl ether, POE 2-octyldodecyl ether and POE cholestanol ether; POE alkyl phenyl ethers such as POE octyl phenyl ether, POE nonyl phenyl ether and POE dinonyl phenyl ether; Pluaronic types such as Pluronic; POE/POP alkyl ethers such as POE/POP cetyl ether, POE/POP 2-decyltetradecyl ether, POE/POP monobutyl ether, POE/POP hydrogenated lanolin and POE/POP glycerin ether; tetra-POE/tetra-POP ethylenediamine condensation products such as Tetronic; POE castor oil hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamic acid monoisostearic acid diester and POE hydrogenated castor oil maleic acid; POE beeswax/lanolin derivatives such as POE sorbitol beeswax; alkanolamides such as coconut oil fatty acid diethanolamide, lauric acid monoethanolamide and fatty acid isopropanol amide; POE propylene glycol fatty acid esters; POE alkylamines; POE fatty acid amides; sucrose fatty acid esters; POE nonylphenyl formaldehyde condensation products; alkyl ethoxy dimethylamine oxides; and trioleyl phosphoric acid.

Examples of other surfactants include anionic surfactants such as fatty acid soaps, higher-alkyl sulfuric ester salts, POE triethanolamine lauryl sulfate, and alkyl ether sulfuric ester salts; cationic surfactants such as alkyl trimethylammonium salts, alkyl pyridinium salts, alkyl quaternary ammonium salts, alkyl dimethylbenzyl ammonium salts, POE alkylamines, alkylamine salts, and polyamine fatty acid derivatives; and amphoteric surfactants such as imidazoline amphoteric surfactants and betaine surfactants. They may be incorporated within the bounds of not causing any problems with stability and skin irritation.

The moisturizer is not particularly limited, and examples thereof may include xylitol, sorbitol, maltitol, chondroitin sulfate, hyaluronic acid, mucoitinsulfuric acid, caronic acid, atelocollagen, cholesteryl-12-hydroxystearate, sodium lactate, bile salts, dl-pyrrolidone carboxylate, short-chain soluble collagens, diglycerol (EO) PO adducts, Rosa roxburghii extract, yarrow extract, and melilot extract.

The higher alcohol is not particularly limited, and examples thereof may include linear alcohols such as lauryl alcohol, cetyl alcohol, stearyl alcohol, behenyl alcohol, myristyl alcohol, oleyl alcohol, and cetostearyl alcohol; and branched alcohols such as monostearyl glycerol ether (batyl alcohol), 2-decyltetradecynol, lanolin alcohol, cholesterol, phytosterol, hexyldodecanol, isostearyl alcohol, and octyldodecanol.

The sequestrant is not particularly limited, and examples thereof may include 1-hydroxyethane-1,1-diphosphonic acid, 1-hydroxyethane-1,1-diphosphonic acid tetrasodium salt, sodium citrate, sodium polyphosphate, sodium metaphosphate, gluconic acid, phosphoric acid, citric acid, ascorbic acid, succinic acid, and edetic acid.

The natural water-soluble polymer is not particularly limited, and examples thereof may include plant-derived polymers such as gum arabic, tragacanth gum, galactan, guar gum, carob gum, karaya gum, carrageenan, pectin, agar, quince seed (quince), algal colloid (algal extract), starch (rice, corn, potato, wheat), and glycyrrhizinic acid; microorganism-derived polymers such as xanthan gum, dextran, succinoglucan, and pullulan; and animal-derived polymers such as collagen, casein, albumin, and gelatin.

The semisynthetic water-soluble polymer is not particularly limited, and examples thereof may include starch polymers such as carboxymethyl starch and methyl hydroxypropyl starch; cellulose polymers such as methyl cellulose, nitro cellulose, ethyl cellulose, methyl hydroxypropyl cellulose, hydroxyethyl cellulose, cellulose sodium sulfate, hydroxypropyl cellulose, sodium carboxymethylcellulose (CMC), crystalline cellulose, and cellulose powder; and alginate polymers such as sodium alginate and propylene glycol alginate.

The synthetic water-soluble polymer is not particularly limited, and examples thereof may include vinyl polymers such as polyvinyl alcohol, polyvinyl methyl ether, and polyvinyl pyrrolidone; polyoxyethylene polymers such as polyethylene glycol 20,000, polyethylene glycol 40,000, and polyethylene glycol 60,000; copolymers such as polyoxyethylene-polyoxypropylene copolymers; acrylic polymers such as sodium polyacrylate, polyethylacrylate, and polyacrylamide; polyethyleneimine; and cationic polymers.

The inorganic water-soluble polymer is not particularly limited, and examples thereof may include bentonite, magnesium aluminum silicate (Veegum), laponite, hectorite, and silicic anhydride.

The ultraviolet blocking agent is not particularly limited, and examples thereof may include benzoic acid-based ultraviolet blocking agents such as paraaminobenzoic acid (hereinafter, abbreviated as PABA), PABA monoglycerin ester, N,N-dipropoxy PABA ethyl ester, N,N-diethoxy PABA ethyl ester, N,N-dimethyl PABA ethyl ester and N,N-dimethyl PABA butyl ester; anthranilic acid-based ultraviolet blocking agents such as homomenthyl-N-acetyl anthranilate; salicylic acid-based ultraviolet blocking agents such as amyl salicylate, menthyl salicylate, homomenthyl salicylate, octyl salicylate, phenyl salicylate, benzyl salicylate and p-isopropanol phenyl salicylate; cinnamic acid-based ultraviolet blocking agents such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate and glycerylmono-2-ethylhexanoyl-di-paramethoxy cinnamate; benzophenone-based ultraviolet blocking agents such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4- methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone and 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenyl benzotriazole, 2-(2'-hydroxy-5'-t-octylphenyl)benzotriazole, 2-(2'-hydroxy-5'-methylphenyl benzotriazole, dibenzalazine, dianisoylmethane, 4-methoxy-4'-t-butyldibenzoylmethane and 5-(3,3-dimethyl-2-norbornylidene)-3-pentane-2-one.

Other chemical components are not particularly limited, and examples thereof may include vitamins such as vitamin A oil, retinol, retinol palmitate, inositol, pyridoxine hydrochloride, benzyl nicotinate, nicotinamide, DL-α-tocopherol nicotinate, magnesium ascorbyl phosphate, 2-O-α-D-glucopyranosyl-L-ascorbic acid, vitamin D2 (ergocalciferol), DL-α-tocopherol, DL-α-tocopherol acetate, pantothenic acid, and biotin; hormones such as estradiol and ethynyl estradiol; amino acids such as arginine, aspartic acid, cystine, cysteine, methionine, serine, leucine, and tryptophan; anti-inflammatory agents such as allantoin and azulene; whitening agents such as arbutin; astringents such as tannic acid; refrigerants such as L-menthol and camphor, sulfur, lysozyme chloride, and pyridoxine chloride.

Various kinds of extracts are not particularly limited, and examples thereof may include Houttuynia cordata extract, Phellodendron bark extract, melilot extract, dead nettle extract, licorice extract, peony root extract, soapwort extract, luffa extract, cinchona extract, strawberry geranium extract, sophora root extract, nuphar extract, fennel extract, primrose extract, rose extract, rehmannia root extract, lemon extract, lithospermum root extract, aloe extract, calamus root extract, eucalyptus extract, field horsetail extract, sage extract, thyme extract, tea extract, seaweed extract, cucumber extract, clove extract, bramble extract, lemon balm extract, carrot extract, horse chestnut extract, peach extract, peach leaf extract, mulberry extract, knapweed extract, hamamelis extract, placenta extract, thymic extract, silk extract, and licorice extract.

Examples of the various kinds of powders may include bright coloring pigments such as red oxide, yellow iron oxide, black iron oxide, mica titanium, iron oxide-coated mica titanium and titanium oxide-coated glass flakes, inorganic powders such as those of mica, talc, kaolin, sericite, titanium dioxide and silica, and organic powders such as polyethylene powder, nylon powder, crosslinked polystyrene, cellulose powder and silicone powder. Preferably, part or all of the powder component is subjected to a hydrophobization treatment with a substance such as a silicone, a fluorine compound, a metallic soap, an oily agent or an acyl glutamic acid salt for improvement of sensory characteristics and improvement of makeup retainability. Other zinc oxide particles that do not fall under the present invention may be mixed and used.

The hexagonal plate-shaped zinc oxide particles of the present invention can also be used as a heat releasing filler.

When the hexagonal plate-shaped zinc oxide particles of the present invention are used as a heat releasing filler, they may be used either alone or in combination with other heat releasing fillers. It is preferable to use the heat releasing filler of the present invention at a ratio of 10 to 90% by volume based on the total amount of a heat releasing composition such as a resin composition or a grease composition regardless of whether it is used alone or used in combination with other heat releasing fillers.

When the hexagonal plate-shaped zinc oxide particles are used as a heat releasing filler, they can be mixed with a resin and used as a heat releasing resin composition. In this case, the resin to be used may be either a thermoplastic resin or a thermosetting resin, and examples thereof may include resins such as an epoxy resin, a phenol resin, a polyphenylene sulfide (PPS) resin, a polyester-based resin, polyamide, polyimide, polystyrene, polyethylene, polypropylene, polyvinyl chloride, polyvinylidene chloride, a fluororesin, polymethyl methacrylate, an ethylene/ethyl acrylate copolymer (EEA) resin, polycarbonate, polyurethane, polyacetal, polyphenylene ether, polyether imide, an acrylonitrile-butadiene-styrene copolymer (ABS) resin, a liquid crystal resin (LCP), a silicone resin and an acrylic resin.

The heat releasing resin composition of the present invention may be a resin composition for thermoforming, which is obtained by kneading a thermoplastic resin and the hexagonal plate-shaped zinc oxide particles in a molten state, or a resin composition obtained by kneading a thermosetting resin and the hexagonal plate-shaped zinc oxide particles, followed by heating the mixture to be cured, or a resin composition for coatings, which is obtained by dispersing the hexagonal plate-shaped zinc oxide particles in a resin solution or dispersion.

The hexagonal plate-shaped zinc oxide particles of the present invention can also be combined with other heat releasing fillers and used as a heat releasing filler composition. Particularly, in the present invention, when the hexagonal plate-shaped zinc oxide particles are used in combination with other heat releasing fillers, all of combination with a heat releasing filler having a larger particle diameter, combination with a heat releasing filler having a smaller particle diameter and combination with heat releasing fillers having larger and smaller particle diameters are conceivable.

The other heat releasing fillers are not particularly limited, and examples thereof may include metal oxides such as zinc oxide, magnesium oxide, titanium oxide and aluminum oxide, aluminum nitride, boron nitride, silicon carbide, silicon nitride, titanium nitride, metal silicon and diamond. When the hexagonal plate-shaped zinc oxide particles of the present invention are used in combination with other heat releasing fillers as described above, it is preferable to include the hexagonal plate-shaped zinc oxide particles at a ratio of 10 to 90% by volume based on the total amount of the heat releasing filler.

When the heat releasing resin composition of the present invention is a resin composition for thermoforming, a resin component can be freely selected according to a use purpose. For example, when the resin composition is bonded and adhered to a heat source and a radiator plate, a resin having high adhesiveness and a low hardness, such as a silicone resin or an acrylic resin, may be selected.

When the heat releasing resin composition of the present invention is a resin composition for coatings, the resin does not necessarily have to have curability. The coating may be a solvent-based coating containing an organic solvent, or a water-based coating with a resin dissolved or dispersed in water.

When the hexagonal plate-shaped zinc oxide particles are used as a heat releasing filler, they can be mixed with a base oil containing a mineral oil or a synthetic oil, and used as a heat releasing grease. When the hexagonal plate-shaped zinc oxide particles are used as the heat releasing grease, an α-olefin, a diester, a polyol ester, a trimellitic acid ester, a polyphenyl ether, an alkyl phenyl ether or the like can be used as a synthetic oil. The hexagonal plate-shaped zinc oxide particles can also be mixed with a silicone oil and used as a heat releasing grease.

When the hexagonal plate-shaped zinc oxide particles of the present invention are used as a heat releasing filler, other components can be used in combination. Examples of other components that can be used in combination may include heat releasing fillers other than zinc oxide, such as metal oxides such as magnesium oxide, titanium oxide and aluminum oxide, aluminum nitride, boron nitride, silicon carbide, silicon nitride, titanium nitride, metal silicon, and diamond; resins; and surfactants.

The hexagonal plate-shaped zinc oxide particles of the present invention can be used in the fields of vulcanization accelerators for rubber, pigments for coatings/inks, electronic components such as ferrites and varistors, pharmaceuticals and so on in addition to the cosmetics and heat releasing fillers described above.

EXAMPLES

Hereinafter, the present invention will be explained with reference to examples. However, the present invention is not limited to these examples.

Example 1

In 1200 ml of an aqueous zinc acetate solution prepared by dissolving 266.07 g of zinc acetate dihydrate (zinc acetate manufactured by Hosoi Chemical Industry Co., Ltd.) in water so as to have a concentration of 1 mol/l in terms of zinc acetate dihydrate, 80 g of FINEX-50 (manufactured by Sakai Chemical Industry Co., Ltd., particle diameter: 0.02 μm) was repulped, thereby forming a slurry. Subsequently, the slurry was heated to 100° C. over 60 minutes with stirring, and aged at 100° C. for 7 hours with stirring. After aging, the slurry was quenched immediately, then filtered and washed with water.

Figure 2:
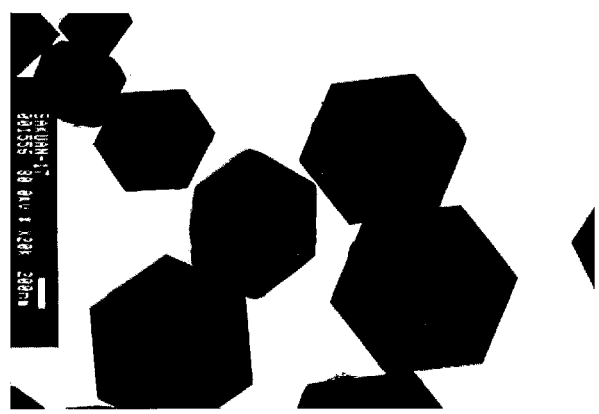
FIG. 2 is a transmission electron microscope photograph of zinc oxide particles of the present invention obtained in Example 1.

Subsequently, the obtained solid was repulped in 3 liters of water to form a slurry, and the slurry was heated to 100° C. over 60 minutes with stirring, and heated and washed at 100° C. for 30 minutes with stirring. After heating and washing, the slurry was filtered, washed with water, and dried at 110° C. for 12 hours to obtain hexagonal plate-shaped zinc oxide particles having a primary particle diameter of 1.12 μm. The size and form of the obtained particles were observed with a scanning electron microscope (SEM, JSM-5600, manufactured by JEOL Ltd.). The obtained electron microscope photograph is shown in FIG. 1. Further, an observation was made with a transmission electron microscope (TEM, JEM-1200EX II, manufactured by JEOL Ltd.). The obtained electron microscope photograph is shown in FIG. 2. The results of evaluating the physical properties of the obtained particles and the physical properties of the coating film are shown in Table 1.

Example 2

In 1200 ml of an aqueous zinc acetate solution prepared by dissolving 266.07 g of zinc acetate dihydrate (zinc acetate manufactured by Hosoi Chemical Industry Co., Ltd.) in water so as to have a concentration of 1 mol/l in terms of zinc acetate dihydrate, 80 g of FINEX-50 (manufactured by Sakai Chemical Industry Co., Ltd., particle diameter: 0.02 μm) was repulped, thereby forming a slurry. Subsequently, the slurry was heated to 100° C. over 60 minutes with stirring, and aged at 100° C. for 3 hours with stirring. After aging, the slurry was quenched immediately, then filtered and washed with water.

Figure 3:
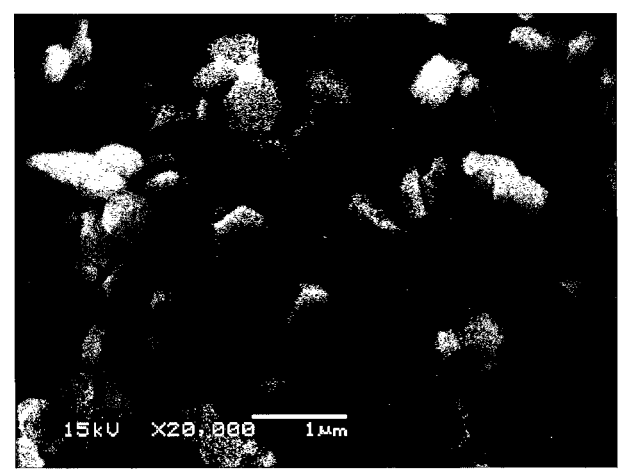
FIG. 3 is a scanning electron microscope photograph of zinc oxide particles of the present invention obtained in Example 2.
Figure 4:
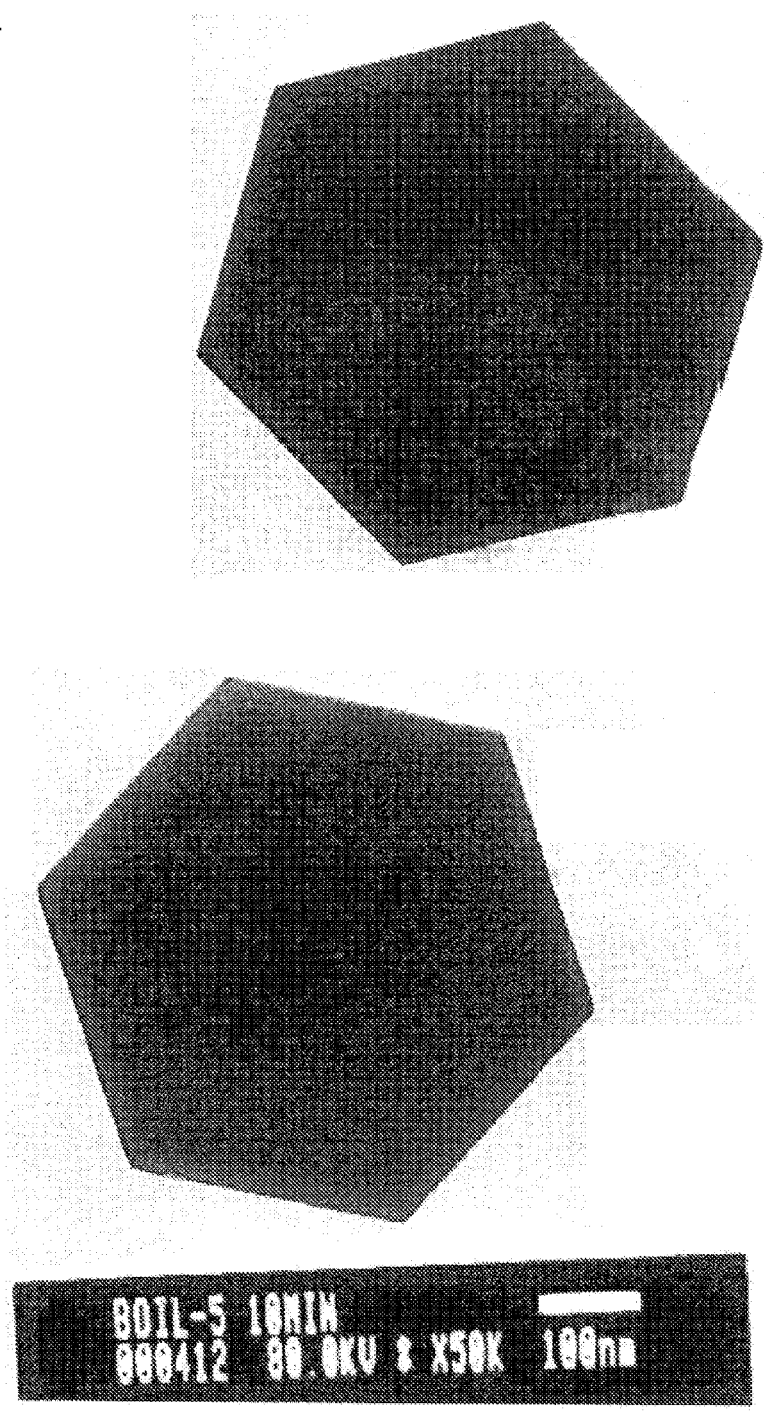
FIG. 4 is a transmission electron microscope photograph of zinc oxide particles of the present invention obtained in Example 2.
Figure 5:
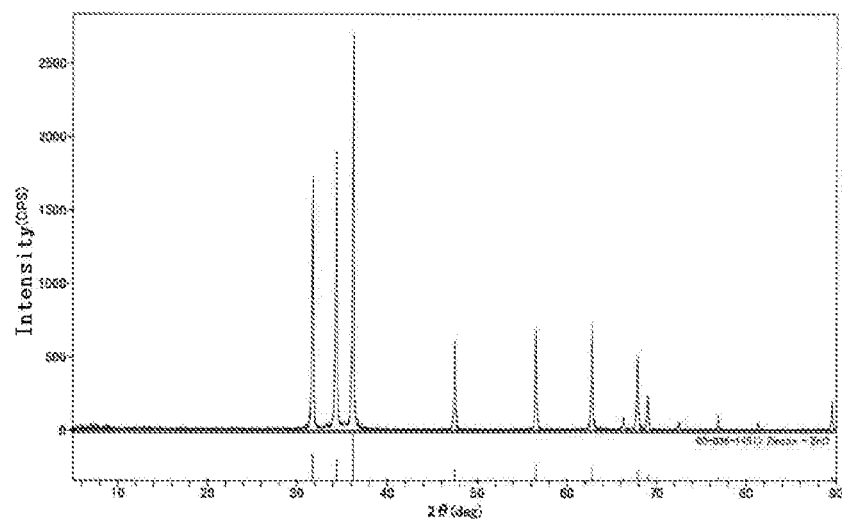
FIG. 5 is an X-ray diffraction spectrum of zinc oxide particles of the present invention obtained in Example 2.

Subsequently, the obtained solid was repulped in 3 liters of water to form a slurry, and the slurry was heated to 100° C. over 60 minutes with stirring, and heated and washed at 100° C. for 30 minutes with stirring. After heating and washing, the slurry was filtered, washed with water, and dried at 110° C. for 12 hours to obtain hexagonal plate-shaped zinc oxide particles having a primary particle diameter of 0.53 μm. The size and form of the obtained particles were observed with a scanning electron microscope (SEM, JSM-5600, manufactured by JEOL Ltd.). The obtained electron microscope photograph is shown in FIG. 3. Further, an observation was made with a transmission electron microscope (TEM, JEM-1200EX II, manufactured by JEOL Ltd.). The obtained electron microscope photograph is shown in FIG. 4. Further, the X-ray diffraction spectrum of the obtained particles is shown in FIG. 5. The results of evaluating the physical properties of the obtained particles and the physical properties of the coating film are shown in Table 1.

Example 3

Figure 6:
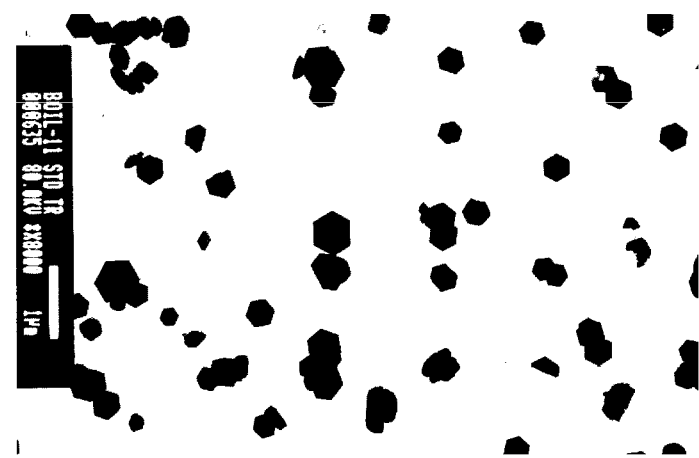
FIG. 6 is a transmission electron microscope photograph of zinc oxide particles of the present invention obtained in Example 3.
Figure 7:
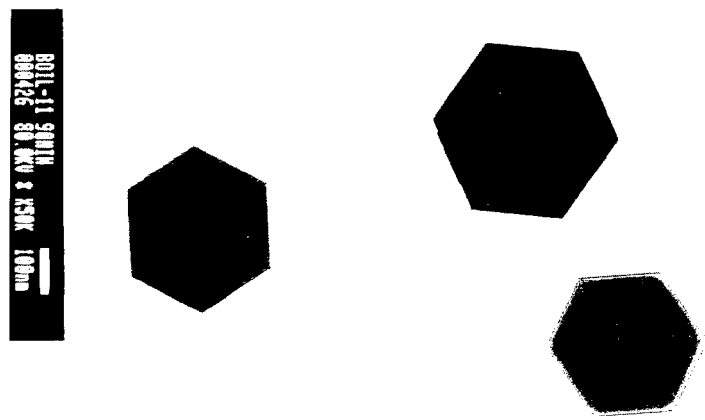
FIG. 7 is a transmission electron microscope photograph of zinc oxide particles of the present invention obtained in Example 3 which are observed with a higher magnification.

In 1200 ml of an aqueous zinc acetate solution prepared by dissolving 266.07 g of zinc acetate dihydrate (zinc acetate manufactured by Hosoi Chemical Industry Co., Ltd.) in water so as to have a concentration of 1 mol/l in terms of zinc acetate dihydrate, 80 g of FINEX-50 (manufactured by Sakai Chemical Industry Co., Ltd., particle diameter: 0.02 μm) was repulped, thereby forming a slurry. Subsequently, the slurry was heated to 100° C. over 60 minutes with stirring, and aged at 100° C. for 1 hour with stirring. After aging, the slurry was quenched immediately, then filtered and washed with water. Subsequently, the obtained solid was repulped in 3 liters of water to form a slurry, and the slurry was heated to 100° C. over 60 minutes with stirring, and heated and washed at 100° C. for 30 minutes with stirring. After heating and washing, the slurry was filtered, washed with water, and dried at 110° C. for 12 hours to obtain hexagonal plate-shaped zinc oxide particles having a primary particle diameter of 0.30 μm. The size and form of the obtained particles were observed with a transmission electron microscope (TEM, JEM-1200EX II, manufactured by JEOL Ltd.). The obtained electron microscope photograph is shown in FIG. 6. Further, an electron microscope photograph with a higher magnification is shown in FIG. 7. The results of evaluating the physical properties of the obtained particles and the physical properties of the coating film are shown in Table 1.

Example 4

Figure 8:
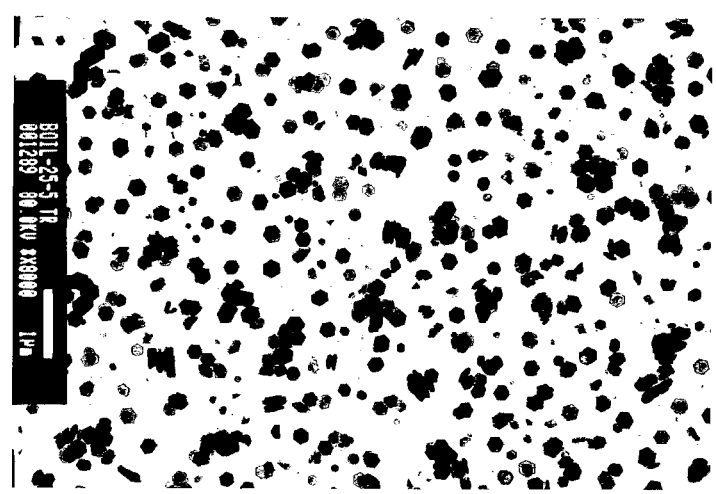
FIG. 8 is a transmission electron microscope photograph of zinc oxide particles of the present invention obtained in Example 4.
Figure 9:
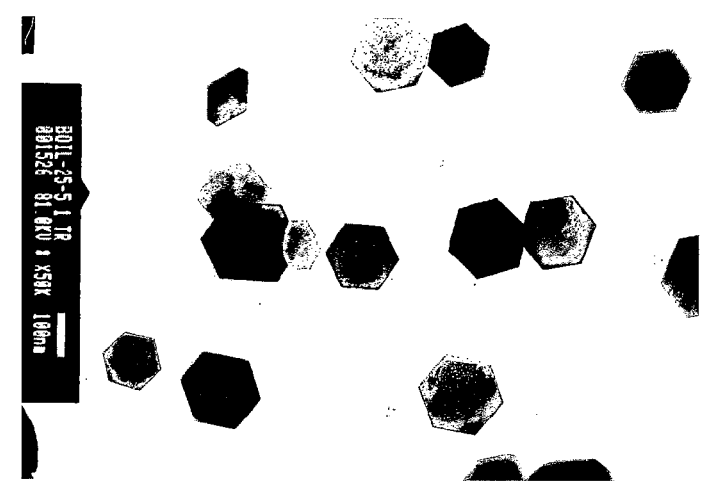
FIG. 9 is a transmission electron microscope photograph of zinc oxide particles of the present invention obtained in Example 4 which are observed with a higher magnification.

In 1200 ml of an aqueous zinc acetate solution prepared by dissolving 133.02 g of zinc acetate dihydrate (zinc acetate manufactured by Hosoi Chemical Industry Co., Ltd.) in water so as to have a concentration of 0.5 mol/l in terms of zinc acetate dihydrate, 80 g of FINEX-50 (manufactured by Sakai Chemical Industry Co., Ltd., particle diameter: 0.02 μm) was repulped, thereby forming a slurry. Subsequently, the slurry was heated to 100° C. over 60 minutes with stirring, and aged at 100° C. for 3 hours with stirring. After aging, the slurry was quenched immediately, then filtered and washed with water. Subsequently, the obtained solid was repulped in 3 liters of water to form a slurry, and the slurry was heated to 100° C. over 60 minutes with stirring, and heated and washed at 100° C. for 30 minutes with stirring. After heating and washing, the slurry was filtered, washed with water, and dried at 110° C. for 12 hours to obtain hexagonal plate-shaped zinc oxide particles having a primary particle diameter of 0.11 μm. The size and form of the obtained particles were observed with a transmission electron microscope (TEM, JEM-1200EX II, manufactured by JEOL Ltd.). The obtained electron microscope photograph is shown in FIG. 8. Further, an electron microscope photograph with a higher magnification is shown in FIG. 9. The results of evaluating the physical properties of the obtained particles and the physical properties of the coating film are shown in Table 1. The crystallite diameter of the plate-shaped surface; (002) plane is 0.07 μm.

Example 5

Figure 10:
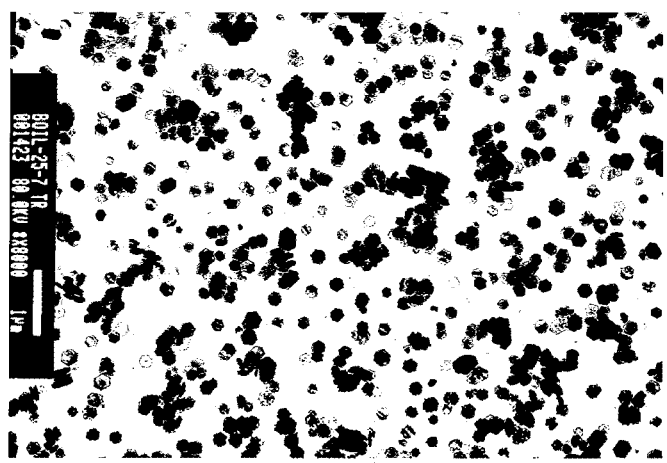
FIG. 10 is a transmission electron microscope photograph of zinc oxide particles of the present invention obtained in Example 5.
Figure 11:
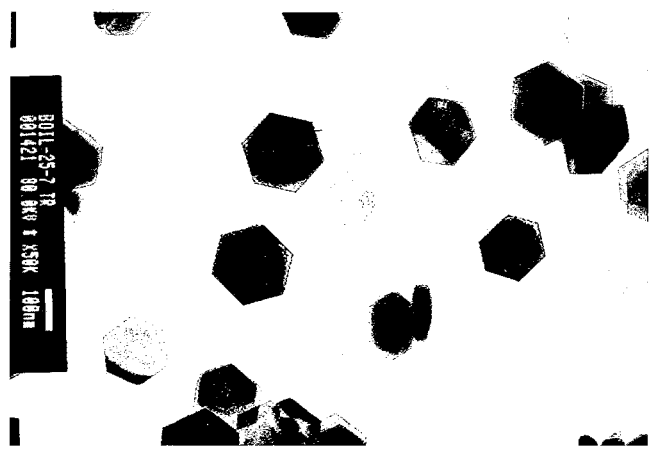
FIG. 11 is a transmission electron microscope photograph of zinc oxide particles of the present invention obtained in Example 5 which are observed with a higher magnification.
Figure 12:
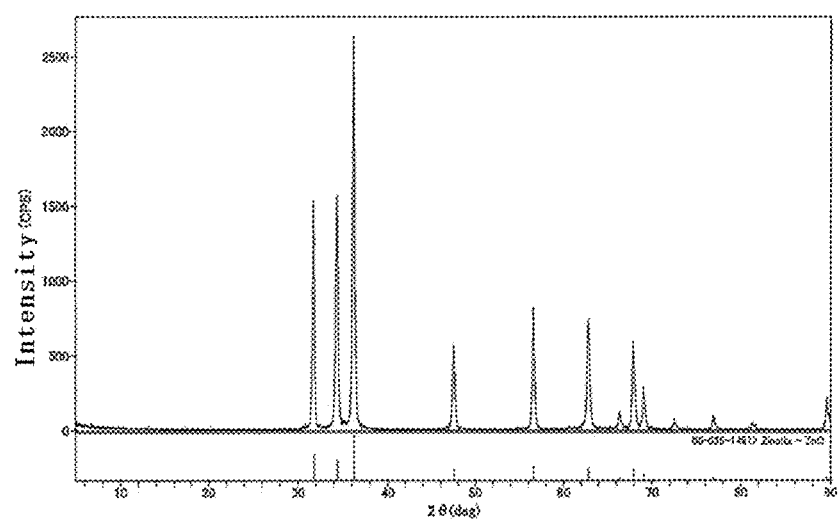
FIG. 12 is an X-ray diffraction spectrum of zinc oxide particles of the present invention obtained in Example 5.

In 1200 ml of an aqueous zinc acetate solution prepared by dissolving 133.02 g of zinc acetate dihydrate (zinc acetate manufactured by Hosoi Chemical Industry Co., Ltd.) in water so as to have a concentration of 0.5 mol/l in terms of zinc acetate dihydrate, 80 g of FINEX-50 (manufactured by Sakai Chemical Industry Co., Ltd., particle diameter: 0.02 μm) was repulped, thereby forming a slurry. Subsequently, the slurry was heated to 70° C. over 42 minutes with stirring, and aged at 70° C. for 3 hours with stirring. After aging, the slurry was quenched immediately, then filtered and washed with water. Subsequently, the obtained solid was repulped in 3 liters of water to form a slurry, and the slurry was heated to 70° C. over 42 minutes with stirring, and heated and washed at 70° C. for 30 minutes with stirring. After heating and washing, the slurry was filtered, washed with water, and dried at 110° C. for 12 hours to obtain hexagonal plate-shaped zinc oxide particles having a primary particle diameter of 0.11 μm. The size and form of the obtained particles were observed with a transmission electron microscope (TEM, JEM-1200EX II, manufactured by JEOL Ltd.). The obtained electron microscope photograph is shown in FIG. 10. Further, an electron microscope photograph with a higher magnification is shown in FIG. 11. Further, the X-ray diffraction spectrum of the obtained particles is shown in FIG. 12. The results of evaluating the physical properties of the obtained particles and the physical properties of the coating film are shown in Table 1. The crystallite diameter of the plate-shaped surface; (002) plane is 0.07 μm.

Comparative Example 1

Figure 13:
FIG. 13 is a transmission electron microscope photograph of zinc oxide particles (Fine zinc oxide manufactured by Sakai Chemical Industry Co., Ltd.) used in Comparative Example 1.

Fine zinc oxide (manufactured by Sakai Chemical Industry Co., Ltd., particle diameter: 0.11 μm) was evaluated in the same manner as in the examples. The electron microscope photograph is shown in FIG. 13. The results of evaluating the physical properties of the obtained particles and the physical properties of the coating film are shown in Table 1.

Comparative Example 2

Figure 14:
FIG. 14 is a transmission electron microscope photograph of zinc oxide particles obtained in Comparative Example 2.

In 1200 ml of water, 80 g of FINEX-50 (manufactured by Sakai Chemical Industry Co., Ltd., particle diameter: 0.02 μm) was repulped to form a slurry. Subsequently, the slurry was heated to 100° C. over 60 minutes with stirring, and aged at 100° C. for 3 hours with stirring. After aging, the slurry was quenched immediately, then filtered, washed with water, and dried at 110° C. for 12 hours to obtain indefinite-shaped zinc oxide particles having a primary particle diameter of 0.02 μm. The size and form of the obtained particles were observed with a transmission electron microscope (TEM, JEM-1200EX II, manufactured by JEOL Ltd.). The obtained electron microscope photograph is shown in FIG. 14. The results of evaluating the physical properties of the obtained particles and the physical properties of the coating film are shown in Table 1.

Comparative Example 3

Figure 15:
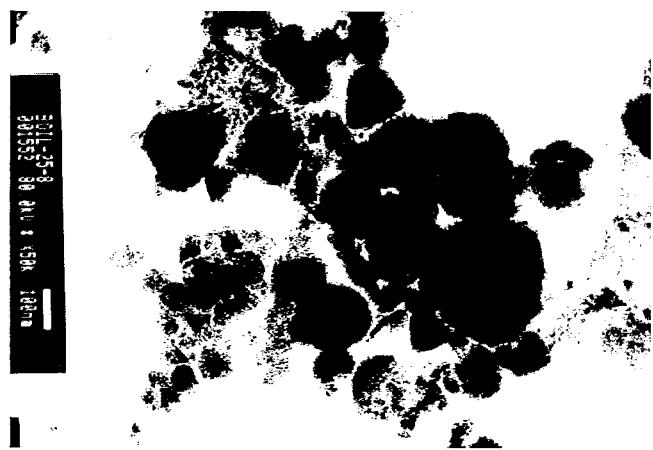
FIG. 15 is a transmission electron microscope photograph of particles obtained in Comparative Example 3.
Figure 16:
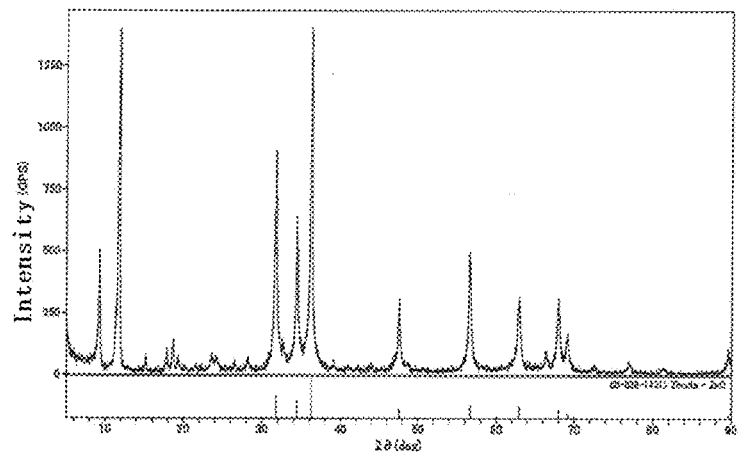
FIG. 16 is an X-ray diffraction spectrum of particles obtained in Comparative Example 3.

In 1200 ml of an aqueous zinc acetate solution prepared by dissolving 133.02 g of zinc acetate dihydrate (zinc acetate manufactured by Hosoi Chemical Industry Co., Ltd.) in water so as to have a concentration of 0.5 mol/l in terms of zinc acetate dihydrate, 80 g of FINEX-50 (manufactured by Sakai Chemical Industry Co., Ltd., particle diameter: 0.02 μm) was repulped, thereby forming a slurry. Subsequently, the slurry was heated to 40° C. over 24 minutes with stirring, and aged at 40° C. for 3 hours with stirring. After aging, the slurry was immediately filtered, and washed with water. Subsequently, the obtained solid was repulped in 3 liters of water to form a slurry, and the slurry was heated to 40° C. over 24 minutes with stirring, and heated and washed at 40° C. for 30 minutes with stirring. After heating and washing, the slurry was filtered, washed with water, and dried at 110° C. for 12 hours to obtain indefinite-shaped zinc oxide particles containing impurities. The size and form of the obtained particles were observed with a transmission electron microscope (TEM, JEM-1200EX II, manufactured by JEOL Ltd.). The obtained electron microscope photograph is shown in FIG. 15. Further, the X-ray diffraction spectrum of the obtained particles is shown in FIG. 16. The results of evaluating the physical properties of the obtained particles and the physical properties of the coating film are shown in Table 1.

Comparative Example 4

Figure 17:
FIG. 17 is a transmission electron microscope photograph of zinc oxide particles obtained in Comparative Example 4.

In an alumina crucible (length/width/height=100 mm/100 mm/35 mm) was put 10 g of FINEX-50 (manufactured by Sakai Chemical Industry Co., Ltd., particle diameter: 0.02 μm), and left standing and calcinated at 675° C. for 2 hours in an electric muffle furnace (manufactured by TOYO ENGINEERING WORKS, LTD.) to obtain indefinite-shaped zinc oxide particles having a primary particle diameter of 0.30 μm. The size and form of the obtained particles were observed with a transmission electron microscope (TEM, JEM-1200EX II, manufactured by JEOL Ltd.). The obtained electron microscope photograph is shown in FIG. 17. The results of evaluating the physical properties of the obtained particles and the physical properties of the coating film are shown in Table 1.

Comparative Example 5

Figure 18:
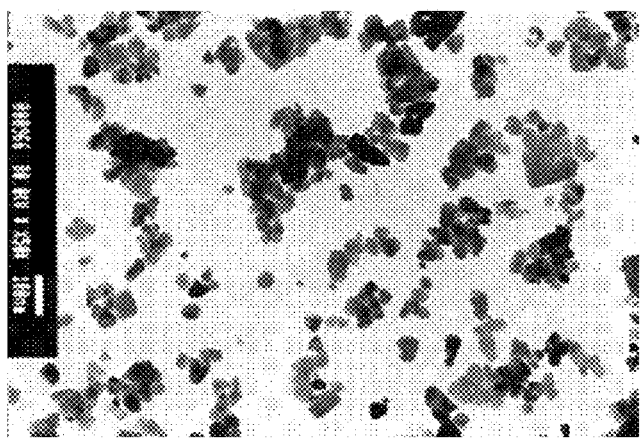
FIG. 18 is a transmission electron microscope photograph of zinc oxide particles obtained in Comparative Example 5.

In 1200 ml of an aqueous zinc acetate solution prepared by dissolving 66.51 g of zinc acetate dihydrate (zinc acetate manufactured by Hosoi Chemical Industry Co., Ltd.) in water so as to have a concentration of 0.25 mol/l in terms of zinc acetate dihydrate, 80 g of FINEX-50 (manufactured by Sakai Chemical Industry Co., Ltd., primary particle diameter: 0.02 μm) was repulped, thereby forming a slurry. Subsequently, the slurry was heated to 70° C. over 42 minutes with stirring, and aged at 70° C. for 3 hours with stirring. After aging, the slurry was immediately filtered, and washed with water. Subsequently, the obtained solid was repulped in 3 liters of water to form a slurry, and the slurry was heated to 70° C. over 42 minutes with stirring, and heated and washed at 70° C. for 30 minutes with stirring. After heating and washing, the slurry was filtered, washed with water, and dried at 110° C. for 12 hours to obtain zinc oxide particles having a primary particle diameter of 0.04 μm. The size and form of the obtained particles were observed with a transmission electron microscope (TEM, JEM-1200EX II, manufactured by JEOL Ltd.). The obtained electron microscope photograph is shown in FIG. 18. The results of evaluating the physical properties of the obtained particles and the physical properties of the coating film are shown in Table 1.

Comparative Example 6

Figure 19:
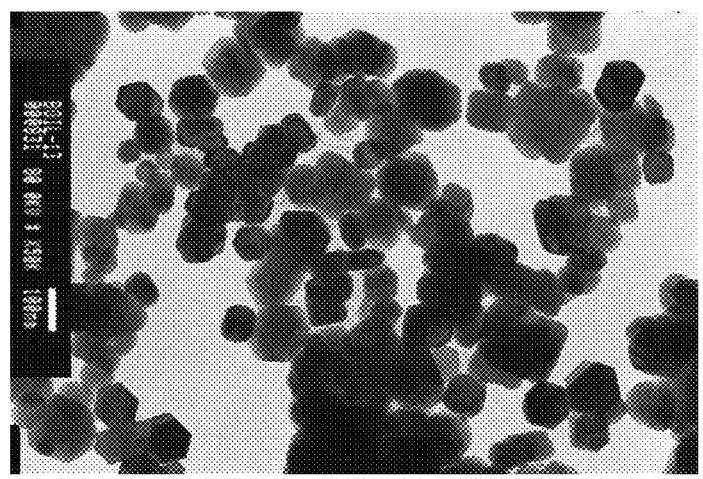
FIG. 19 is a transmission electron microscope photograph of zinc oxide particles obtained in Comparative Example 6.

In 1200 ml of an aqueous zinc acetate solution prepared by dissolving 106.42 g of zinc acetate dihydrate (zinc acetate manufactured by Hosoi Chemical Industry Co., Ltd.) in water so as to have a concentration of 0.4 mol/l in terms of zinc acetate dihydrate, 80 g of SF-15 (zinc oxide fine particles manufactured by Sakai Chemical Industry Co., Ltd., particle diameter: 0.08 μm) was repulped, thereby forming a slurry. Subsequently, the slurry was heated to 70° C. over 42 minutes with stirring, and aged at 70° C. for 5 hours with stirring. After aging, the slurry was immediately filtered, and washed with water. Subsequently, the obtained solid was repulped in 3 liters of water to form a slurry, and the slurry was heated to 70° C. over 42 minutes with stirring, and heated and washed at 70° C. for 30 minutes with stirring. After heating and washing, the slurry was filtered, washed with water, and dried at 110° C. for 12 hours to obtain hexagonal prism-shaped zinc oxide particles having a primary particle diameter of 0.12 μm. The size and form of the obtained particles were observed with a transmission electron microscope (TEM, JEM-1200EX II, manufactured by JEOL Ltd.). The obtained electron microscope photograph is shown in FIG. 19. The results of evaluating the physical properties of the obtained particles and the physical properties of the coating film are shown in Table 1.

Comparative Example 7

Figure 20:
FIG. 20 is a transmission electron microscope photograph of zinc oxide particles (FINEX-50 manufactured by Sakai Chemical Industry Co., Ltd.) used in Comparative Example 7.

FINEX-50 (manufactured by Sakai Chemical Industry Co., Ltd., particle diameter: 0.02 μm) was evaluated in the same manner as in the examples. The electron microscope photograph is shown in FIG. 20. The results of evaluating the physical properties of the obtained particles and the physical properties of the coating film are shown in Table 1.

Comparative Example 8

Figure 21:
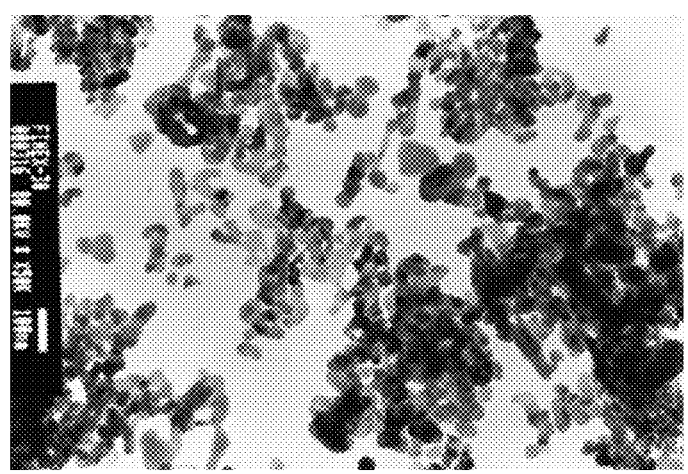
FIG. 21 is a transmission electron microscope photograph of zinc oxide particles (FINEX-30 manufactured by Sakai Chemical Industry Co., Ltd.) used in Comparative Example 8.

FINEX-30 (manufactured by Sakai Chemical Industry Co., Ltd., particle diameter: 0.04 μm) was evaluated in the same manner as in the examples. The electron microscope photograph is shown in FIG. 21. The results of evaluating the physical properties of the obtained particles and the physical properties of the coating film are shown in Table 1.

TABLE 1

| | | Example 1 | Example 2 | Example 3 | Example 4 | Example 5 | Comparative Example 1 | Comparative Example 2 |
|---|---|---|---|---|---|---|---|---|
| Preparation conditions | Zinc oxide fine particles as raw material | FINEX-50 | FINEX-50 | FINEX-50 | FINEX-50 | FINEX-50 | Fine zinc oxide | FINEX-50 |
| | Particle diameter of raw material (μm) | 0.02 | 0.02 | 0.02 | 0.02 | 0.02 | 0.11 | 0.02 |
| | Amount of raw material used in preparation (g) | 80 | 80 | 80 | 80 | 80 | | 80 |
| | Zinc salt used in preparation | Zinc acetate dihydrate | Zinc acetate dihydrate | Zinc acetate dihydrate | Zinc acetate dihydrate | Zinc acetate dihydrate | | |
| | Amount of zinc salt (g) | 266.07 | 266.07 | 266.07 | 133.02 | 133.02 | | |
| | Solvent used in preparation | Water | Water | Water | Water | Water | | Water |
| | Amount of aqueous zinc salt solution (ml) | 1200 | 1200 | 1200 | 1200 | 1200 | | 1200 |
| | Concentration of aqueous zinc salt solution (mol/l) | 1 | 1 | 1 | 0.5 | 0.5 | | |
| | Aging temperature (° C.) | 100 | 100 | 100 | 100 | 70 | | 100 |
| | Aging time (Hr) | 7 | 3 | 1 | 3 | 3 | | 3 |
| | Calcinating temperature/calcinating time | | | | | | | |
| Physical properties of particles | Composition of obtained particles | Zinc oxide | Zinc oxide | Zinc oxide | Zinc oxide | Zinc oxide | Zinc oxide | Zinc oxide |
| | Particle shape | Hexagonal plate shape | Hexagonal plate shape | Hexagonal plate shape | Hexagonal plate shape | Hexagonal plate shape | Indefinite shape | Indefinite shape |
| | Primary particle diameter (μm) | 1.12 | 0.53 | 0.30 | 0.11 | 0.11 | 0.11 | 0.02 |
| | Crystallite diameter (μm) | | | | 0.07 | 0.07 | | |
| | Crystalllite diameter/primary particle diameter | | | | 0.64 | 0.64 | | |
| | Aspect ratio | 3.4 | 3.6 | 3.7 | 3.4 | 3.5 | | |
| | Ratio (%) of particles, in 250 particles, which satisfy requirements (1) and (2) in claim 1 | 73 | 69 | 72 | 68 | 70 | | |
| | Average value of Dmin/Dmax measured for 250 particles observed in terms of a hexagonal-shaped surface | 0.97 | 0.98 | 0.97 | 0.96 | 0.97 | | |
| | Powder touch | 5 | 4 | 3 | 3 | 3 | 2 | |
| Physical properties of coating film | Total light transmittance 1 (%) | | 43 | 19 | 12 | 13 | 20 | |
| | Total light transmittance 2 (%) | | 41 | 16 | 9 | 10 | 17 | |
| | Total light transmittance 3 (%) | | 43 | 18 | 10 | 11 | 15 | |
| | Parallel light transmittance 1 (%) | | 20 | 17 | 54 | 55 | 53 | |
| | Parallel light transmittance 2 (%) | | 47 | 49 | 81 | 83 | 79 | |
| | Total light transmittance 4 (%) | 85 | 83 | 77 | 80 | 80 | 81 | |
| | Haze (%) | 61 | 63 | 63 | 27 | 27 | 26 | |

TABLE 1-continued

|  |  | Comparative Example 3 | Comparative Example 4 | Comparative Example 5 | Comparative Example 6 | Comparative Example 7 | Comparative Example 8 |
|---|---|---|---|---|---|---|---|
| Preparation conditions | Zinc oxide fine particles as raw material | FINEX-50 | FINEX-50 | FINEX-50 | SF-15 | FINEX-50 | FINEX-30 |
|  | Particle diameter of raw material (μm) | 0.02 | 0.02 | 0.02 | 0.08 | 0.02 | 0.04 |
|  | Amount of raw material used in preparation (g) | 80 | 10 | 80 | 80 |  |  |
|  | Zinc salt used in preparation | Zinc acetate dihydrate |  | Zinc acetate dihydrate | Zinc acetate dihydrate |  |  |
|  | Amount of zinc salt (g) | 133.02 |  | 66.51 | 106.42 |  |  |
|  | Solvent used in preparation | Water |  | Water | Water |  |  |
|  | Amount of aqueous zinc salt solution (ml) | 1200 |  | 1200 | 1200 |  |  |
|  | Concentration of aqueous zinc salt solution (mol/l) | 0.5 |  | 0.25 | 0.4 |  |  |
|  | Aging temperature (° C.) | 40 |  | 70 | 70 |  |  |
|  | Aging time (Hr) | 3 |  | 3 | 5 |  |  |
|  | Calcinating temperature/calcinating time |  | 675° C./2 Hr |  |  |  |  |
| Physical properties of particles | Composition of obtained particles | Zinc oxide containing impurities | Zinc oxide | Zinc oxide | Zinc oxide | Zinc oxide | Zinc oxide |
|  | Particle shape | Indefinite shape | Indefinite shape | Indefinite shape | Hexagonal prism shape | Indefinite shape | Indefinite shape |
|  | Primary particle diameter (μm) |  | 0.30 | 0.04 | 0.12 | 0.02 | 0.04 |
|  | Crystallite diameter (μm) |  |  |  |  |  |  |
|  | Crystalllite diameter/primary particle diameter |  |  |  |  |  |  |
|  | Aspect ratio |  |  | 1.3 | 1.2 | 1.8 | 2.0 |
|  | Ratio (%) of particles, in 250 particles, which satisfy requirements (1) and (2) in claim 1 |  |  |  |  |  |  |
|  | Average value of Dmin/Dmax measured for 250 particles observed in terms of a hexagonal-shaped surface |  |  |  |  |  |  |
|  | Powder touch |  | 2 | 2 | 2 | 1 | 1 |
| Physical properties of coating film | Total light transmittance 1 (%) |  | 41 | 14 | 12 | 15 | 13 |
|  | Total light transmittance 2 (%) |  | 37 | 13 | 10 | 16 | 13 |
|  | Total light transmittance 3 (%) |  | 32 | 28 | 10 | 54 | 24 |
|  | Parallel light transmittance 1 (%) |  | 37 | 84 | 56 | 85 | 78 |
|  | Parallel light transmittance 2 (%) |  | 63 | 93 | 81 | 93 | 90 |
|  | Total light transmittance 4 (%) |  | 78 |  |  |  |  |
|  | Haze (%) |  | 58 |  |  |  |  |

(Composition of Obtained Particles)

The X-ray diffraction spectra shown in FIGS. 5, 12 and 16 and the compositions of the obtained particles in Table 1 show results of performing analysis using an X-ray diffractometer UltimaIII (manufactured by Rigaku Corporation) having an X-ray tube with copper. From these results, it is evident that zinc oxide was obtained in the examples. It is evident that the zinc oxide particles of Comparative Example 3 contain impurities.

(Aspect Ratio)

The aspect ratio of the hexagonal plate-shaped zinc oxide particles of the examples was measured by the measurement method described above.

For the aspect ratio of the zinc oxide particles having an indefinite particle shape in comparative examples, a major axis of the indefinite-shaped zinc oxide particle and a minor axis passing through the center of the major axis are measured in a visual field of 2000 to 50000 magnification in a transmission electron microscope (TEM, JEM-1200EX II, manufactured by JEOL Ltd.) photograph, and a ratio between the lengths of the major axis and the minor axis: major axis/minor axis is determined. The ratio of major axis/minor axis is measured in the manner described above for 250 indefinite-shaped zinc oxide particles in the TEM photograph, and an average value of a cumulative distribution thereof is determined as an aspect ratio. The method for measurement of an aspect ratio of indefinite-shaped zinc oxide particles is shown in FIG. 26.

The aspect ratio of the zinc oxide particles having a hexagonal prism particle shape in the comparative example is determined in the following manner. For the aspect ratio of the hexagonal prism-shaped zinc oxide particles, a major axis and a minor axis are measured for particles in which the side surface of the hexagonal prism-shaped zinc oxide particle faces frontward (particles observed as a rectangular or square shape) in a visual field of 2000 to 50000 magnification in a transmission electron microscope (TEM, JEM-1200EX II, manufactured by JEOL Ltd.) photograph, and a ratio between the lengths of the major axis and the minor axis: major axis/minor axis is determined. The ratio of major axis/minor axis is measured in the manner described above for 250 hexagonal prism-shaped zinc oxide particles in the TEM photograph, and an average value of a cumulative distribution thereof is determined as an aspect ratio. Hexagonal prism-shaped zinc oxide particles in which the hexagonal-shaped surface faces frontward were excluded from measurement objects because it was difficult to determine the thickness. The method for measurement of an aspect ratio of hexagonal prism-shaped zinc oxide particles is shown in FIG. 25.

(Crystallite Diameter)

For the crystallite diameter (μm) herein, results of performing analysis using an X-ray diffractometer UltimaIII (manufactured by Rigaku Corporation) having an X-ray tube with copper-are shown. The crystallite usually means a small single crystal in a microscopic level, which forms a crystalline substance. Herein, the crystallite diameter (μm) is a value determined from a half width of a diffraction peak of the plate-shaped surface: (002) plane of zinc oxide in the X-ray diffraction pattern of a hexagonal wurtzite-type zinc oxide particle.

(Crystallite Diameter/Primary Particle Diameter)

A value shown as crystallite diameter/primary particle diameter herein is a value as an indicator of a level of independency of primary particles that form a powder. As described previously, the primary particle diameter is a particle diameter (μm) defined by a unidirectional particle diameter in a visual field of 2000 to 50000 magnification in a transmission electron microscope (TEM, JEM-1200EX II, manufactured by JEOL Ltd.) photograph (distance between two parallel lines in a fixed direction with a particle held therebetween; measurements are made in a fixed direction regardless of shapes of particles on the image), and is a geometric particle diameter obtained by measuring the unidirectional diameters of 250 primary particles in the TEM photograph and determining an average value of a cumulative distribution thereof. On the other hand, the crystallite diameter is a value determined from a half width of a diffraction peak of the plate-shaped surface: (002) plane of zinc oxide in the X-ray diffraction pattern as described previously. Therefore, as the value of crystallite diameter/primary particle diameter becomes closer to 1, a difference between the geometric particle diameter and the single crystal size decreases, which means that primary particles are not aggregated particles, but exist independently as single crystal particles. The values of crystallite diameter/primary particle diameter of the hexagonal plate-shaped zinc oxide particles obtained in Examples 4 and 5 are both 0.64, and therefore primary particles are not aggregated particles but rather single crystals.

(Powder Touch)

The powder touch herein is an indicator showing slippage and roughness in a touch felt when a small amount of a powder is placed on the skin and the powder is drawn by a finger. Herein, score evaluations are performed in five grades with score 5 given when slippage is very good and no roughness is felt, score 4 given when slippage is good and almost no roughness is felt, score 3 given when both slippage and roughness are moderate, score 2 given when slippage is poor and roughness is felt, and score 1 given when slippage is very poor and roughness is felt. The results are shown in Table 1. A higher score means a better powder touch, and particles having a better powder touch can be more suitably used in applications of foundations and other makeup cosmetics.

(Preparation of Coating Film)

In a mayonnaise bottle having a volume of 75 ml, 2 g of zinc oxide particles obtained in each of examples and comparative examples described above, 10 g of varnish (ACRYDIC A-801-P manufactured by DIC Corporation), 5 g of butyl acetate (special grade reagent, manufactured by Wako Pure Chemical Industries, Ltd.), 5 g of xylene (genuine special grade, manufactured by JUNSEI CHEMICAL CO., LTD.) and 38 g of glass beads (1.5 mm, manufactured by Potters-Ballotini Co., Ltd.) were put and sufficiently mixed, then fixed in a paint conditioner Model 5410 (manufactured by RED DEVIL, Inc.), and subjected to a dispersion treatment by giving vibrations for 90 minutes, thereby preparing a coating. Next, a small amount of the prepared coating was added dropwise onto a slide glass (length/width/thickness=76 mm/26 mm/0.8 to 1.0 mm, manufactured by Matsunami Glass Ind., Ltd.), and a coating film was prepared using a bar coater (No. 579 ROD No. 6, manufactured by YASUDA SEIKI SEISAKUSHO, LTD.). The prepared coating film was dried at 20° C. for 12 hours, and then used for measurement of total light transmittance 1, total light transmittance 2, total light transmittance 3, parallel light transmittance 1, parallel light transmittance 2 and haze.

(Total Light Transmittance 1, Total Light Transmittance 2, Total Light Transmittance 3, Parallel Light Transmittance 1 and Parallel Light Transmittance 2)

Herein, total light transmittance 1(%), total light transmittance 2(%), total light transmittance 3(%), parallel light transmittance 1(%) and parallel light transmittance 2(%) are values obtained by measuring the prepared coating film using a spectrophotometer V-570 (manufactured by JASCO Corporation). The value of total light transmittance 1(%) is a value of total light transmittance at a wavelength of 310 nm, the value of total light transmittance 2(%) is a value of total light transmittance at a wavelength of 350 nm, the value of total light transmittance 3(%) is a value of total light transmittance at a wavelength of 375 nm, the value of parallel light transmittance 1(%) is a value of parallel light transmittance at a wavelength of 500 nm, and the value of parallel light transmittance 2(%) is a value of parallel light transmittance at a wavelength of 700 nm. An ultraviolet blocking effect to ultraviolet rays having a wavelength of UVB is enhanced as the value of total light transmittance 1(%) becomes smaller, and an ultraviolet blocking effect to ultraviolet rays having a wavelength of UVA is enhanced as the values of total light transmittance 2(%) and total light transmittance 3(%) become smaller. Particularly, when the value of total light transmittance 3(%) is small, a blocking region to ultraviolet rays having a wavelength of UVA extends over a wider range. Visible light transparency is enhanced as the values of parallel light transmittance 1(%) and parallel light transmittance 2(%) become larger.

(Total Light Transmittance 4 and Haze)

The total light transmittance 4(%) and haze (%) in Table 1 are values obtained by measuring the prepared coating film using a haze meter HM-150 (manufactured by MURAKAMI COLOR RESEARCH LABORATORY CO., Ltd.). When coating films having comparable values of total light transmittance 4(%) are compared, those having a higher haze (%) have a higher effect of blurring a base (a so called soft focus effect).

From Table 1 above, it is evident that the hexagonal plate-shaped zinc oxide particles of the present invention show a proper powder touch with good slippage and no roughness when the primary particle diameter is 0.5 μm or more. It is evident that the hexagonal plate-shaped zinc oxide particles have a high haze and hence an excellent soft focus effect when the primary particle diameter is 0.3 μm or more. It is evident that particularly the particles of Examples 1 and 2 are zinc oxide particles having both a proper powder touch and a proper soft focus effect. It is evident that when the primary particle diameter is 0.3 μm or less, total light transmittance 1 and total light transmittance 2 are low, so that excellent ultraviolet blocking performance is shown. It is evident that particularly the particles of Example 3 are zinc oxide particles having both an excellent soft focus effect and excellent ultraviolet blocking performance, and also have an excellent powder touch as compared to the indefinite-shaped zinc oxide particles of Comparative Example 4 having a comparable primary particle diameter. It is evident that when the primary particle diameter is about 0.1 μm, parallel light transmittance 1 and parallel light transmittance 2 are high, so that excellent visible light transparency is shown. It is evident that particularly the particles of Examples 4 and 5 are zinc oxide particles having both excellent ultraviolet blocking performance and excellent visible light transparency, and also have an excellent powder touch as compared to the indefinite-shaped zinc oxide particles of Comparative Example 1 having a comparable primary particle diameter. Further, it is evident that the particles of Examples 4 and 5 have low total light transmittance 3, and have excellent ultraviolet blocking performance in a wavelength range of UVA at 375 nm. On the other hand, for the zinc oxide particles of Comparative Example 7 having a primary particle diameter of 0.02 μm and the zinc oxide particles of Comparative Example 8 having a primary particle diameter of 0.04 μm, sufficient ultraviolet blocking performance could not be achieved in a wavelength range of UVA at 375 nm. The hexagonal plate-shaped zinc oxide particles of the present invention could not be obtained under the conditions of Comparative Examples 2, 3, 5 and 6, which fell out of the conditions of the production method of the present invention.

INDUSTRIAL APPLICABILITY

The hexagonal plate-shaped zinc oxide particles of the present invention can be used as a component of a cosmetic, a heat releasing filler, a heat releasing resin composition, a heat releasing grease and a heat releasing coating composition.

The invention claimed is:

1. Hexagonal plate-shaped zinc oxide particles having hexagonal-shaped surfaces, wherein
   the primary particle diameter is 0.01 μm or more and the aspect ratio is 2.5 or more, and
   50% or more of 250 particles in a transmission electron microscope photograph satisfy both the requirements (1) and (2):
   (1) the particle has a hexagonal-shaped surface; and
   (2) Dmin/Dmax 0.3, where
   Dmax: a length of the largest diagonal line of three diagonal lines of the hexagonal-shaped surface of the hexagonal plate-shaped zinc oxide particle; and
   Dmin: a length of the smallest diagonal line of three diagonal lines of the hexagonal-shaped surface of the hexagonal plate-shaped zinc oxide particle, and
   wherein the aspect ratio of the hexagonal plate-shaped zinc oxide particles is a value determined as a ratio of L/T where L is an average value of measured particle diameters (μm) of 250 particles, the particle diameter defined by a unidirectional diameter for particles in which the hexagonal-shaped surface of the hexagonal plate-shaped zinc oxide particle faces frontward (distance between two parallel lines in a fixed direction with a particle held there between; measurements are made in a fixed direction for particles in which the hexagonal-shaped surface on the image faces frontward), and T is an average value of measured thicknesses (μm) (length of the shorter dimension of the side surface of the particles) of 250 particles for particles in which the side surface of the hexagonal plate-shaped zinc oxide particle faces frontward, in a visual field of 2000 to 50000 magnification in a transmission electron microscope photograph or a scanning electron microscope photograph.

2. The hexagonal plate-shaped zinc oxide particles according to claim 1, which are obtained by aging zinc oxide fine particles in an aqueous zinc salt solution,
   wherein the zinc salt concentration in the aqueous zinc salt solution is more than 0.45 mol/l and 4.00 mol/l or less and the aging is performed at 45 to 110° C.

3. A method for production of the hexagonal plate-shaped zinc oxide particles according to claim 2, comprising a step of aging zinc oxide fine particles in an aqueous zinc salt solution,
   wherein the zinc salt concentration in the aqueous zinc salt solution is more than 0.45 mol/l and 4.00 mol/l or less and the aging is performed at 45 to 110° C.

4. A cosmetic comprising the hexagonal plate-shaped zinc oxide particles according to claim 2.

5. A heat releasing filler comprising the hexagonal plate-shaped zinc oxide particles according to claim 2.

6. A heat releasing resin composition comprising the hexagonal plate-shaped zinc oxide particles according to claim 2.

7. A heat releasing grease comprising the hexagonal plate-shaped zinc oxide particles according to claim 2.

8. A heat releasing coating composition comprising the hexagonal plate-shaped zinc oxide particles according to claim 2.

9. A method for production of the hexagonal plate-shaped zinc oxide particles according to claim 1, comprising a step of aging zinc oxide fine particles in an aqueous zinc salt solution,
   wherein the zinc salt concentration in the aqueous zinc salt solution is more than 0.45 mol/l and 4.00 mol/l or less and the aging is performed at 45 to 110° C.

10. A cosmetic comprising the hexagonal plate-shaped zinc oxide particles according to claim 1.

11. A heat releasing filler comprising the hexagonal plate-shaped zinc oxide particles according to claim 1.

12. A heat releasing resin composition comprising the hexagonal plate-shaped zinc oxide particles according to claim 1.

13. A heat releasing grease comprising the hexagonal plate-shaped zinc oxide particles according to claim 1.

14. A heat releasing coating composition comprising the hexagonal plate-shaped zinc oxide particles according to claim 1.

* * * * *